US008022046B2

(12) United States Patent
Brown et al.

(10) Patent No.: US 8,022,046 B2
(45) Date of Patent: Sep. 20, 2011

(54) MICROSPHERE-BASED COMPOSITION FOR PREVENTING AND/OR REVERSING NEW-ONSET AUTOIMMUNE DIABETES

(75) Inventors: Larry R. Brown, Newton, MA (US); Nick Giannoukakis, Coraopolis, PA (US); Massimo Trucco, Pittsburgh, PA (US)

(73) Assignees: Baxter International, Inc., Deerfield, IL (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 9 days.

(21) Appl. No.: 12/426,904

(22) Filed: Apr. 20, 2009

(65) Prior Publication Data
US 2009/0291145 A1 Nov. 26, 2009

Related U.S. Application Data

(60) Provisional application No. 61/046,034, filed on Apr. 18, 2008, provisional application No. 61/048,246, filed on Apr. 28, 2008.

(51) Int. Cl.
*C12N 15/11* (2006.01)
*C07H 21/02* (2006.01)
*C07H 21/04* (2006.01)

(52) U.S. Cl. ..... 514/44; 536/23.1; 536/24.3; 536/24.33; 536/24.5

(58) Field of Classification Search ............ 536/24.5; 514/44
See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts'o et al. |
| 4,476,301 | A | 10/1984 | Imbach et al. |
| 4,530,840 | A | 7/1985 | Tice et al. |
| 4,845,205 | A | 7/1989 | Huynh Dinh et al. |
| 4,897,268 | A | 1/1990 | Tice et al. |
| 4,904,479 | A | 2/1990 | Illum |
| 4,981,957 | A | 1/1991 | Lebleu et al. |
| 5,023,243 | A | 6/1991 | Tullis |
| 5,034,506 | A | 7/1991 | Summerton et al. |
| 5,075,109 | A | 12/1991 | Tice et al. |
| 5,102,872 | A | 4/1992 | Singh et al. |
| 5,118,800 | A | 6/1992 | Smith et al. |
| 5,130,302 | A | 7/1992 | Spielvogel et al. |
| 5,134,066 | A | 7/1992 | Rogers et al. |
| 5,149,543 | A | 9/1992 | Cohen et al. |

(Continued)

FOREIGN PATENT DOCUMENTS
EP 0248531 12/1987
(Continued)

OTHER PUBLICATIONS

Englisch et al., Chemically modified oligonucleotides as probes and inhibitors. *Angew. Chem. Int. Ed.* 30(6): 613-722 (1991). Freier et al., The ups and downs of nucleic acid duplex stability: structure-stability studies on chemically-modified DNA:RNA duplexes. *Nucl. Acids Res.* 25: 4429-43 (1997).

(Continued)

*Primary Examiner* — Sean McGarry
*Assistant Examiner* — Terra C. Gibbs
(74) *Attorney, Agent, or Firm* — Marshall, Gerstein & Borun LLP

(57) ABSTRACT

A method is provided that includes using an antisense approach to reverse and/or delay an autoimmune diabetes condition in vivo. The oligonucleotides are targeted to bind to primary transcripts CD40, CD80, CD86 and their combinations.

15 Claims, 28 Drawing Sheets

U.S. PATENT DOCUMENTS

| | | | |
|---|---|---|---|
| 5,166,315 A | 11/1992 | Summerton et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,312,812 A | 5/1994 | Balazs et al. |
| 5,319,080 A | 6/1994 | Leumann |
| 5,321,131 A | 6/1994 | Agrawal et al. |
| 5,359,044 A | 10/1994 | Cook et al. |
| 5,360,610 A | 11/1994 | Tice et al. |
| 5,367,066 A | 11/1994 | Urdea et al. |
| 5,384,133 A | 1/1995 | Boyes et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,417,986 A | 5/1995 | Reid et al. |
| 5,432,272 A | 7/1995 | Benner |
| 5,434,257 A | 7/1995 | Matteucci et al. |
| 5,446,137 A | 8/1995 | Maag et al. |
| 5,453,966 A | 9/1995 | Aramaki |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,578,709 A | 11/1996 | Woiszwillo |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,599,719 A | 2/1997 | Woiszwillo et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 5,981,719 A | 11/1999 | Woiszwillo et al. |
| 6,005,096 A | 12/1999 | Matteucci et al. |
| 6,090,925 A | 7/2000 | Woiszwillo et al. |
| 6,268,053 B1 | 7/2001 | Woiszwillo et al. |
| 6,458,387 B1 | 10/2002 | Scott et al. |
| 2004/0192899 A1* | 9/2004 | Sharpe et al. ............ 530/388.22 |
| 2004/0219565 A1 | 11/2004 | Kauppinen et al. |
| 2006/0024240 A1 | 2/2006 | Brown et al. |

FOREIGN PATENT DOCUMENTS

| | | |
|---|---|---|
| WO | WO 9523859 A2 * | 8/1995 |
| WO | WO-98/39352 | 9/1998 |
| WO | WO-99/14226 | 3/1999 |
| WO | WO 9953953 A2 * | 10/1999 |
| WO | WO-00/74687 | 12/2000 |
| WO | WO-2008/109495 | 9/2008 |

OTHER PUBLICATIONS

Gmyr et al., Human pancreatic ductal cells: large-scale isolation and expansion. *Cell Transplant.* 10: 109-21 (2001).

Medarova et al., Imaging beta-cell death with a near-infrared probe. *Diabetes.* 54: 1780-8 (2005).

Mesmaeker et al., Backbone modifications in oligonucleotides and peptide nucleic acid systems. *Curr. Opin. Struct. Biol.* 5: 343-55 (1995).

Nielsen et al., Sequence-selective recognition of DNA by strand displacement with a thymine-substituted polyamide. *Science.* 254: 1497-1500 (1991).

Petrovsky et al., Near-infrared fluorescent imaging of tumor apoptosis. *Cancer Res.* 63: 1936-42 (2003).

Thornton et al., CD4+CD25+ immunoregulatory T cells suppress polyclonal T cell activation in vitro by inhibiting interleukin 2 production. *J. Exp. Med.* 188: 287-96 (1998).

Thornton et al., Suppressor effector function of CD4+CD25+ immunoregulatory T cells is antigen nonspecific. *J. Immunol.* 164: 183-90 (2000).

Geneseq Databas Accession No. AAF32882, Human B7-2 mRNA antisense oligonucleotide SEQ ID: 79, Mar. 23, 2001.

Geneseq Databas Accession No. AT004050, Human CD40 mRNA target sequence for mRNA, SEQ ID: 1306, Nov. 27, 2008.

Geneseq Database Accession No. AAF32883, Human B7-2 mRNA antisense oligonucleotide SEQ ID No. 80, Mar. 23, 2001.

Geneseq Database Accession No. AAF33175, Human B7-2 antisense oligonucleotide SEQ ID No. 259, Mar. 23, 2001.

Giannoukakis et al., Toward a cure for type 1 diabetes mellitus: Diabetes-suppressive dendritic cells and beyond. *Ped. Diabetes*, 9(3): 4-13 (2008).

Machen et al., Antisense oligonucleotides down-regulating costimulation confer diabetes-preventive properties to nonobese diabetic mouse dendritic cells. *J. Immunol.* 173: 4331-41 (2004).

Phillips et al., A microsphere-based vaccine prevents and reverses new-onset autoimmune diabetes. *Diabetes*, 57(6): 1544-55 (2008).

International Search Report, PCT/US2009/41167, European Patent Office, dated Aug. 19, 2009.

* cited by examiner

*Figure 6A*
DIABETIC NOD
H+E
*Figure 6C*
SCR-MSP NOD
(HYPERGLYCEMIC)
INSULIN STAINING
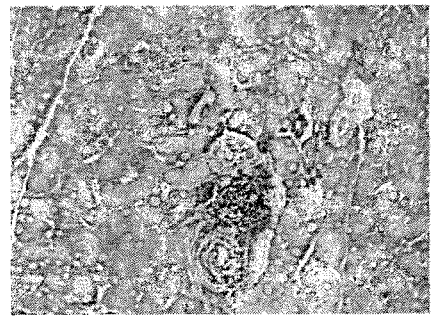
DIABETIC NOD
*Figure 6B*
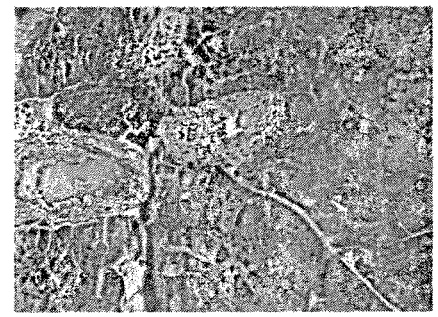
SCR-MSP NOD
(HYPERGLYCEMIC)
*Figure 6D*

Figure 7A
ASMSP-TREATED DIABETES-FREE
NOD MICE (Tx < 8 WEEKS OF AGE)
H+E
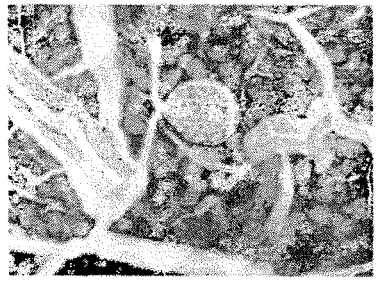
INSULIN
Figure 7B
Figure 7C
AS-ODN DC-TREATED
DIABETES-FREE NOD MICE (Tx 10 TIMES
FOLLOWING DIABETES ONSET)
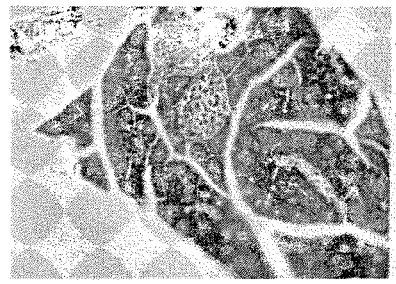
Figure 7D

SPLENIC T-CELLS

POOLED LYMPH NODE T-CELLS

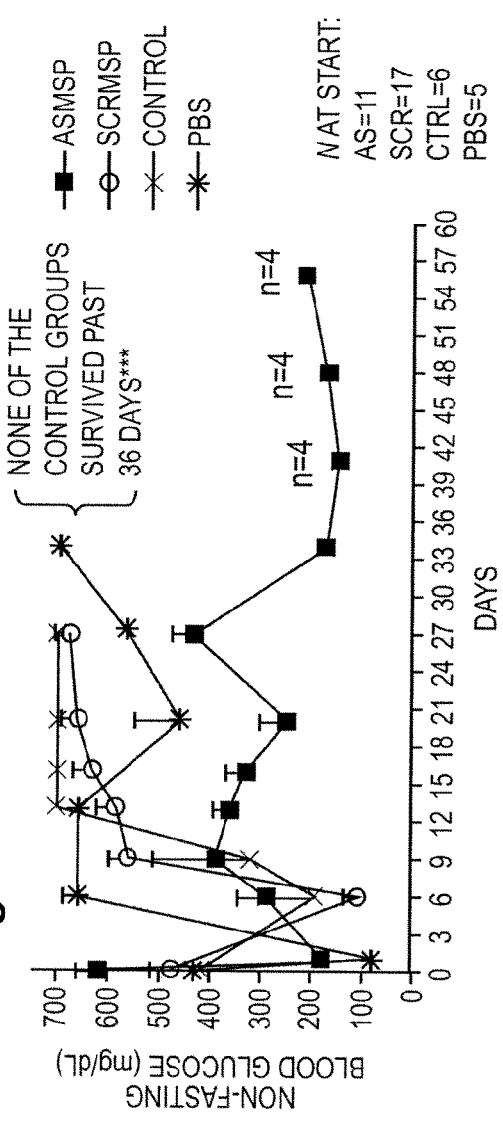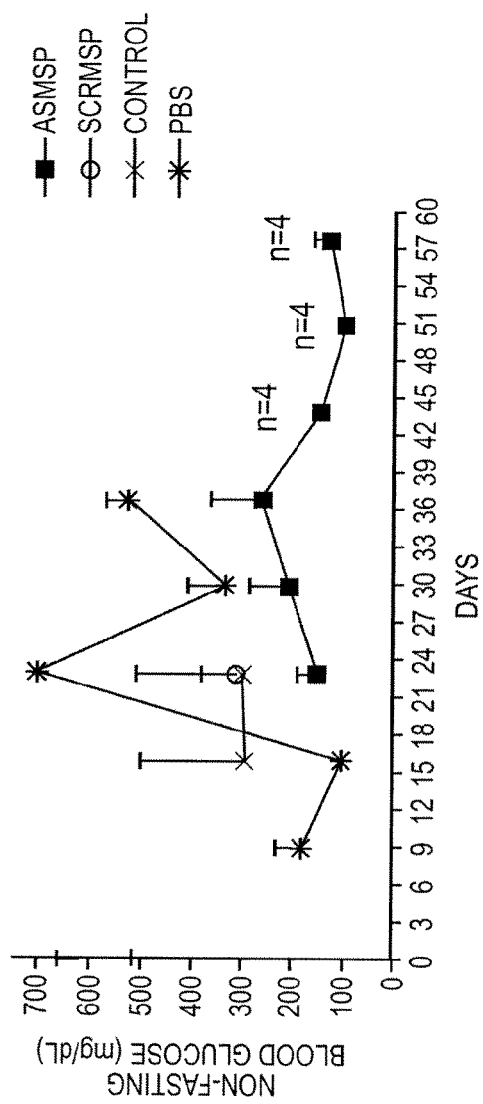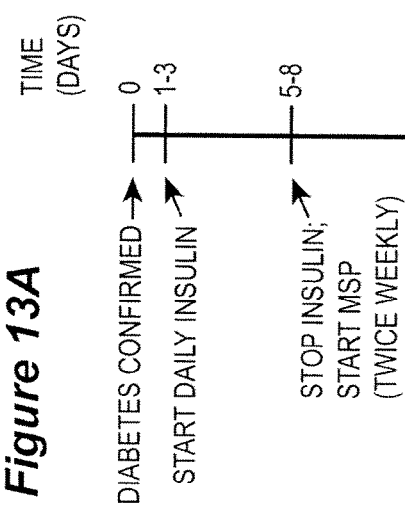

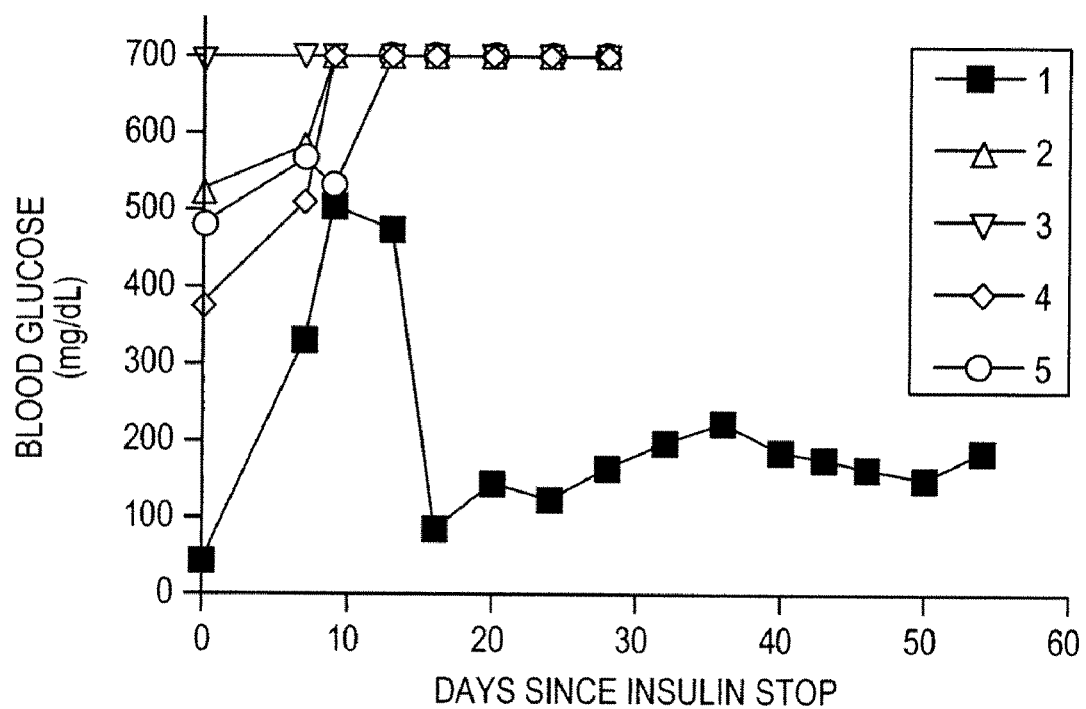

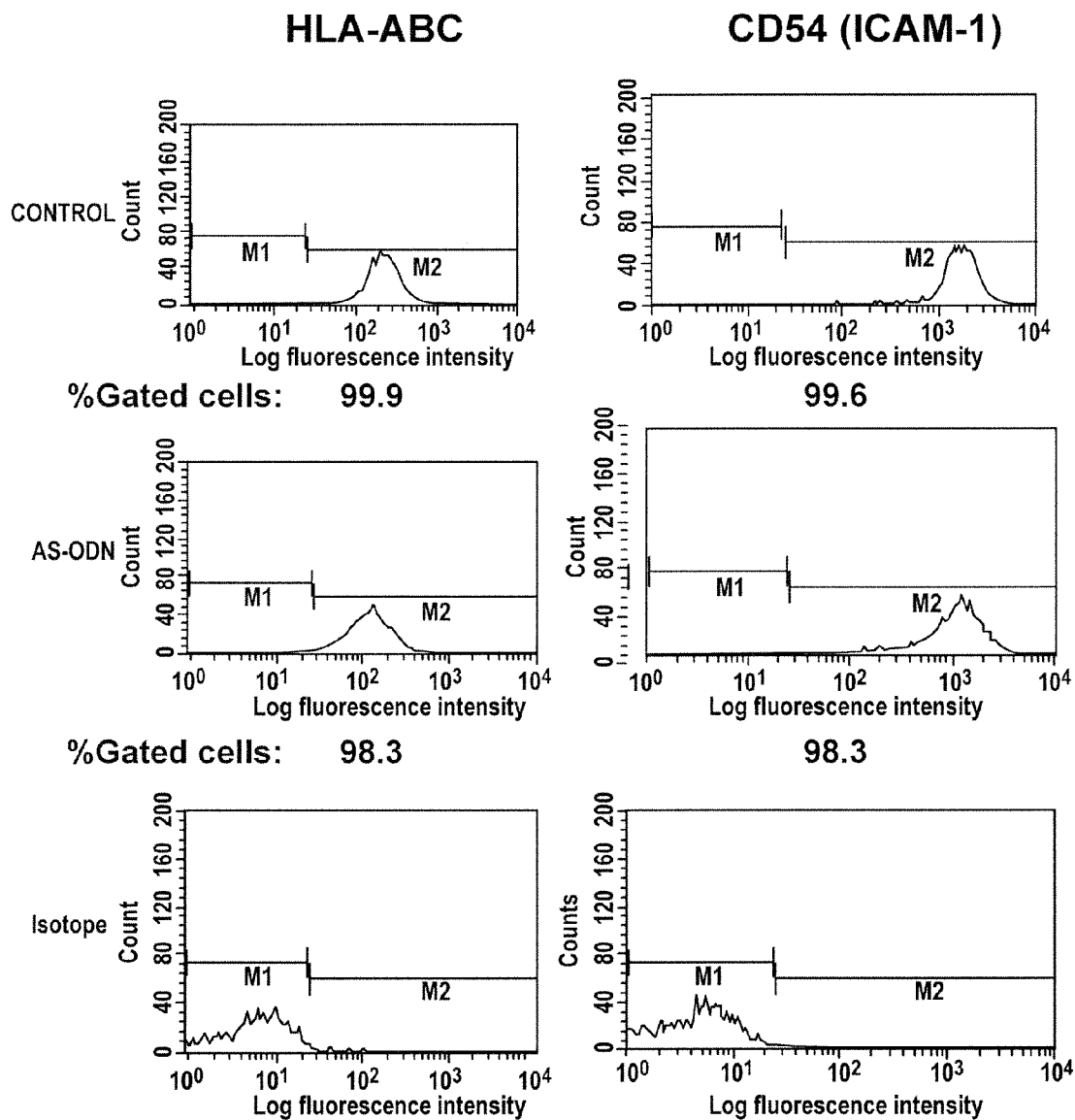
Figure 16C (cont'd 1)

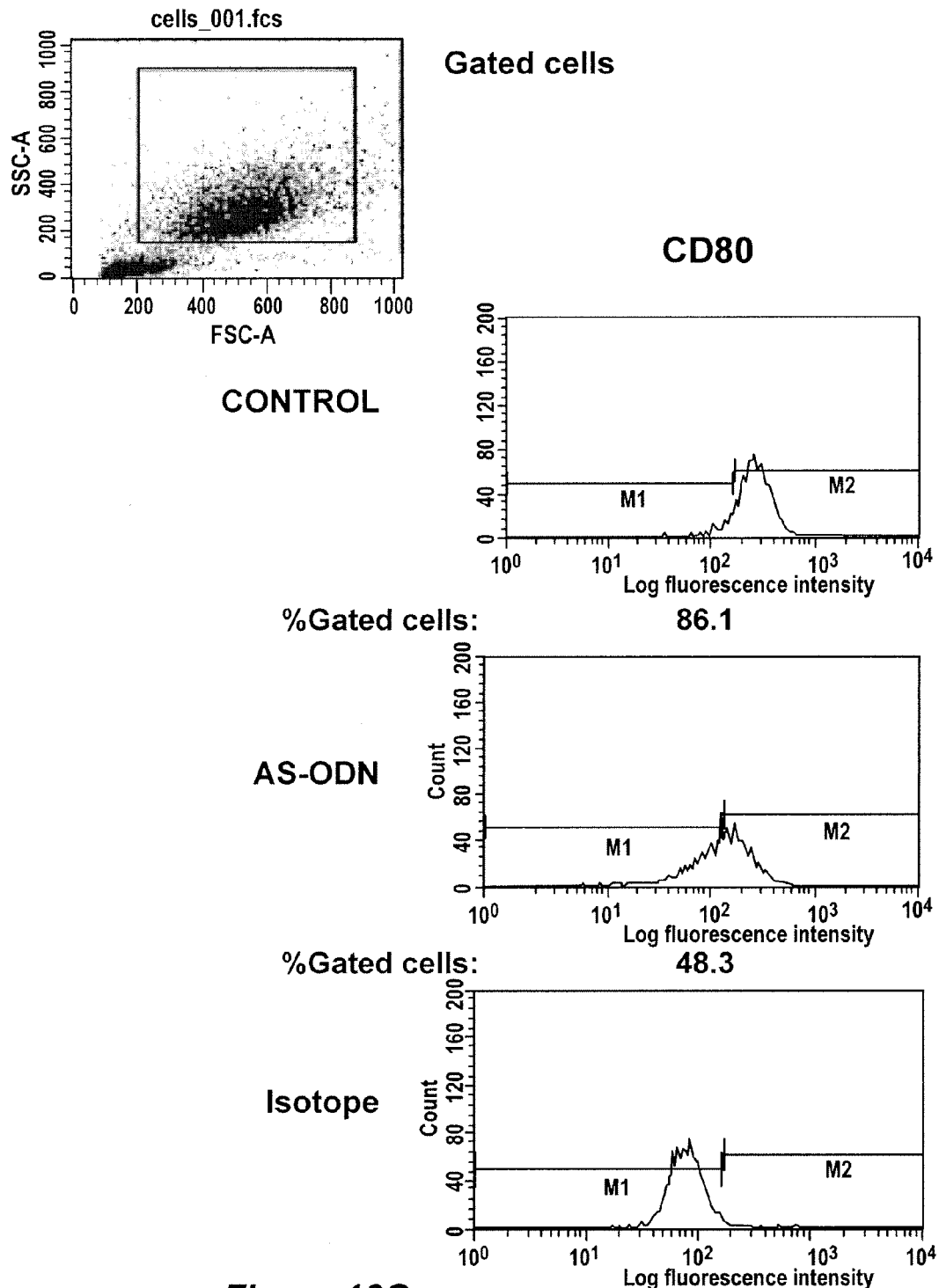
Figure 16C (cont'd 2)

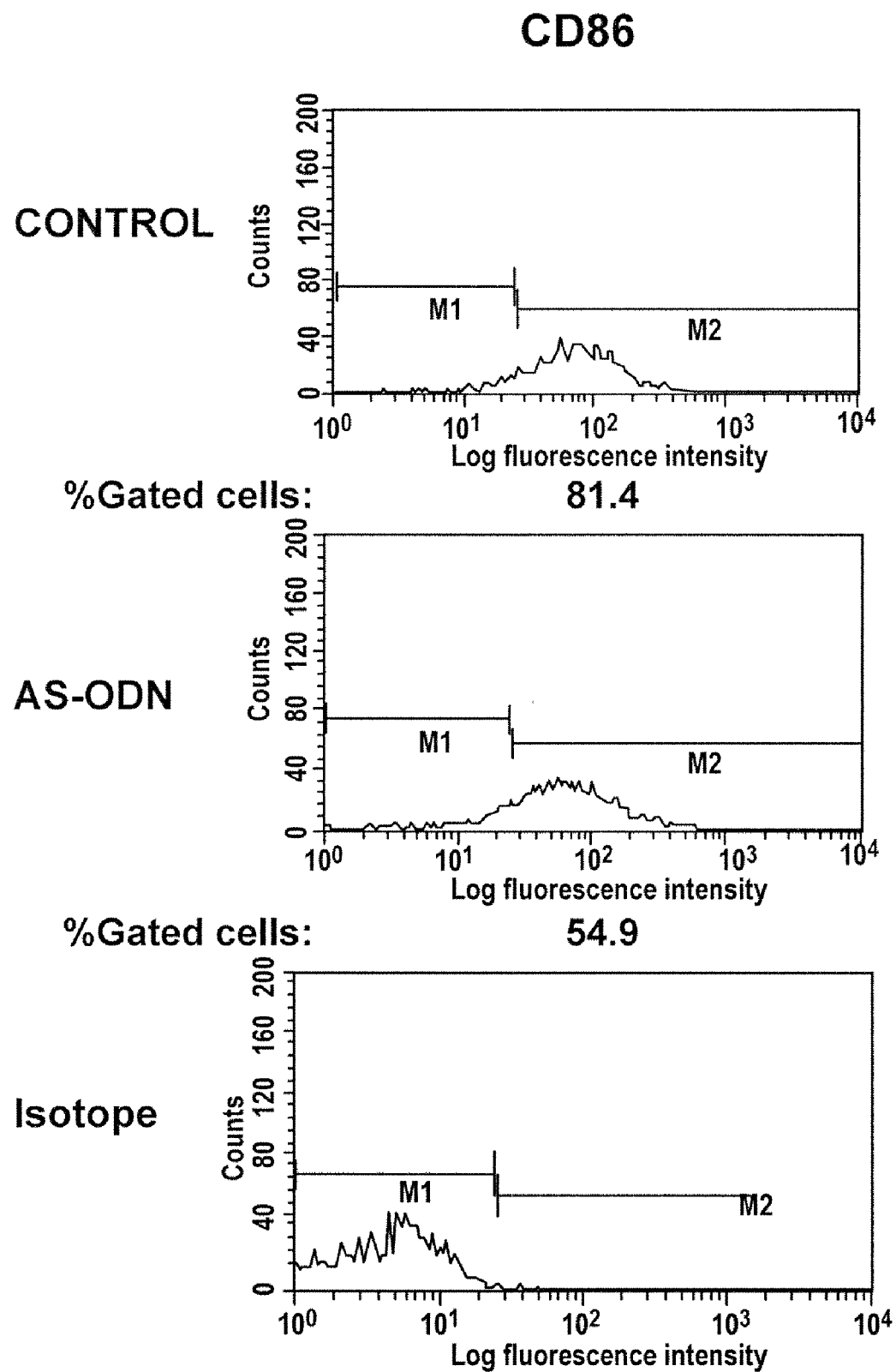
Figure 16C (cont'd 3)

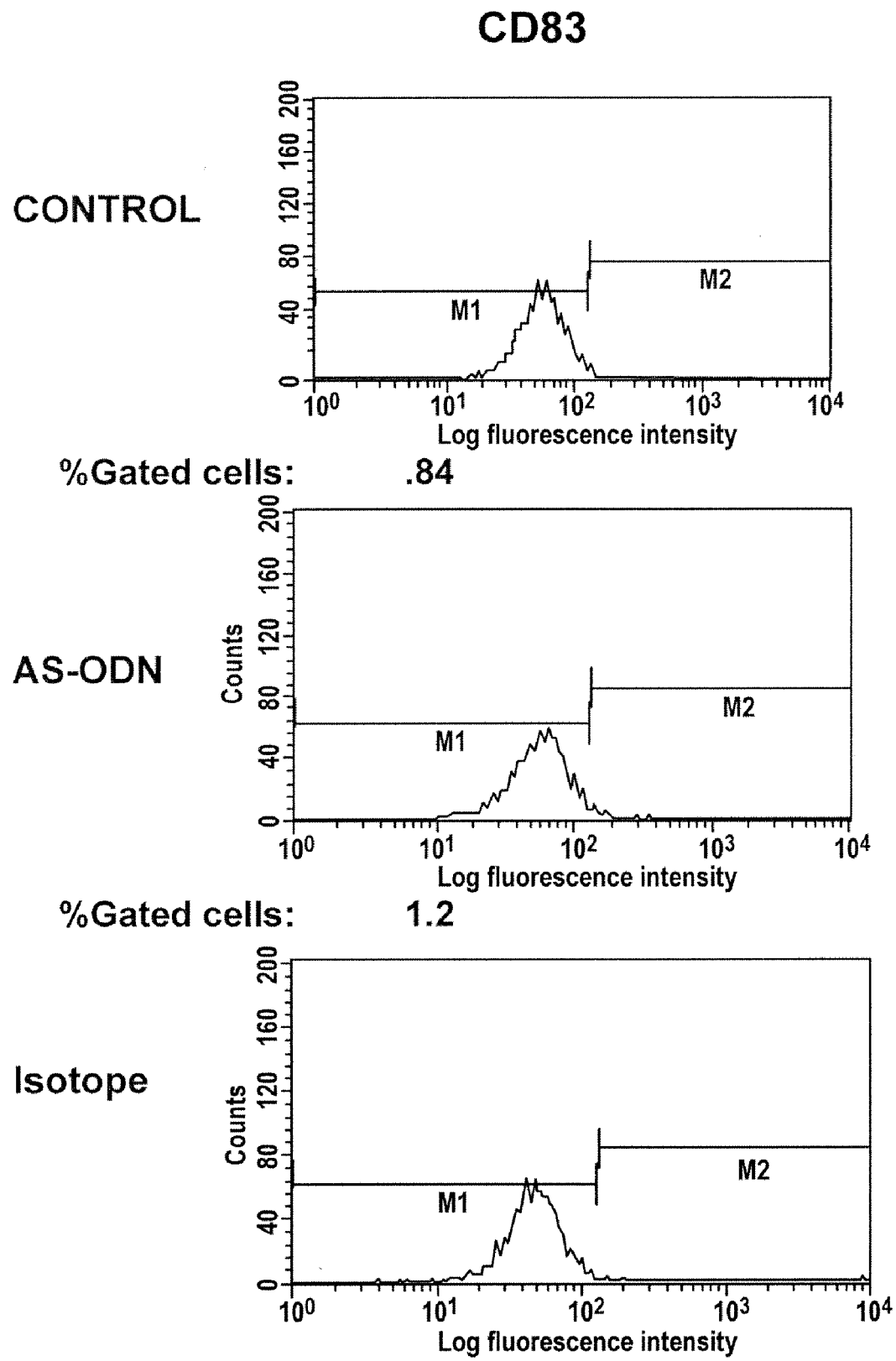
Figure 16C (cont'd 4)

Proliferation of T-cells from a healthy human volunteer, recently administered a tetanus booster vaccine, co-cultured with autologous AS-ODN-treated peripheral blood-derived DC in the presence of tetanus toxoid. Error bars indicate the standard error of the mean of the response from three independent co-cultures of cells of the same individual.

Proliferation of T-cells from healthy human volunteers co-cultured with autologous AS-ODN-treated peripheral blood-derived DC in the presence or absence of intact ovalbumin as nominal antigen. Error bars indicate the standard error of the mean of the response from three independent volunteers.

Proliferation of T-cells from healthy human volunteers co-cultured with allogeneic AS-ODN-treated peripheral blood-derived DC or untreated allogeneic DC. Error bars indicate the standard error of the mean of the response from three independent volunteers where the DC donor remained the same.

SEQUENCE LISTING

<160> NUMBER OF SEQ ID NOS: 20

<210> SEQ ID NO 1
<211> LENGTH: 31
<212> TYPE: DNA
<213> ORGANISM: Mus musculus

<400> SEQUENCE: 1
cacagccgag gcaaagacac catgcagggc a                                    31

```
<210> SEQ ID NO 2
<211> LENGTH: 29
<212> TYPE: DNA
<213> ORGANISM: Mus musculus

<400> SEQUENCE: 2
gggaaagcca ggaatctaga gccaatgga                                     29

<210> SEQ ID NO 3
<211> LENGTH: 30
<212> TYPE: DNA
<213> ORGANISM: Mus musculus

<400> SEQUENCE: 3
tgggtgcttc cgtaagttct ggaacacgtc                                    30

<210> SEQ ID NO 4
<211> LENGTH: 30
<212> TYPE: DNA
<213> ORGANISM: Homo sapiens

<400> SEQUENCE: 4
actgggcgcc cgagcgaggc ctctgctgac                                    30

<210> SEQ ID NO 5
<211> LENGTH: 30
<212> TYPE: DNA
<213> ORGANISM: Homo sapiens

<400> SEQUENCE: 5
ttgctcacgt agaagaccct cccagtgatg                                    30

<210> SEQ ID NO 6
<211> LENGTH: 30
<212> TYPE: DNA
<213> ORGANISM: Homo sapiens

<400> SEQUENCE: 6
aaggagtatt tgcgagctcc ccgtacctcc                                    30

<210> SEQ ID NO 7
<211> LENGTH: 29
<212> TYPE: DNA
<213> ORGANISM: Homo sapiens

<400> SEQUENCE: 7
ttgctcacgt agaagaccct ccagtgatg                                     29

<210> SEQ ID NO 8
<211> LENGTH: 23
<212> TYPE: DNA
<213> ORGANISM: Homo sapiens

<400> SEQUENCE: 8
acaatccaat tgctcacgta gaa                                           23

<210> SEQ ID NO 9
<211> LENGTH: 19
<212> TYPE: DNA
<213> ORGANISM: Homo sapiens

<400> SEQUENCE: 9
ttgctcacgt agaagaccc                                                19
```

```
<210> SEQ ID NO 10
<211> LENGTH: 19
<212> TYPE: DNA
<213> ORGANISM: Homo sapiens

<400> SEQUENCE: 10
ttgggaaact ggtgtgttg                                                  19

<210> SEQ ID NO 11
<211> LENGTH: 23
<212> TYPE: DNA
<213> ORGANISM: Homo sapiens

<400> SEQUENCE: 11
agattaaggt aatggcccag gat                                             23

<210> SEQ ID NO 12
<211> LENGTH: 19
<212> TYPE: DNA
<213> ORGANISM: Mus musculus

<400> SEQUENCE: 12
tattactgcg ccgaatcct                                                  19

<210> SEQ ID NO 13
<211> LENGTH: 20
<212> TYPE: DNA
<213> ORGANISM: Rattus norvegicus

<400> SEQUENCE: 13
cggttcttgt actcgggcca                                                 20

<210> SEQ ID NO 14
<211> LENGTH: 19
<212> TYPE: DNA
<213> ORGANISM: Rattus norvegicus

<400> SEQUENCE: 14
gtccggttct tgtactcgg                                                  19

<210> SEQ ID NO 15
<211> LENGTH: 19
<212> TYPE: DNA
<213> ORGANISM: Homo sapiens

<400> SEQUENCE: 15
ttggagaaga agccgactg                                                  19

<210> SEQ ID NO 16
<211> LENGTH: 19
<212> TYPE: DNA
<213> ORGANISM: Homo sapiens

<400> SEQUENCE: 16
ctgcactgag atgcgactc                                                  19

<210> SEQ ID NO 17
<211> LENGTH: 19
<212> TYPE: DNA
<213> ORGANISM: Rattus norvegicus

<400> SEQUENCE: 17
agatgcgact ctctttgcc                                                  19
```

```
<210> SEQ ID NO 18
<211> LENGTH: 23
<212> TYPE: DNA
<213> ORGANISM: Homo sapiens

<400> SEQUENCE: 18
caaaatacta ctagctcact cag                                              23

<210> SEQ ID NO 19
<211> LENGTH: 19
<212> TYPE: DNA
<213> ORGANISM: Homo sapiens

<400> SEQUENCE: 19
tggtcctgcc aaaatacta                                                   19

<210> SEQ ID NO 20
<211> LENGTH: 19
<212> TYPE: DNA
<213> ORGANISM: Homo sapiens

<400> SEQUENCE: 20
cagttctgtg acattatct                                                   19
```

MICROSPHERE-BASED COMPOSITION FOR PREVENTING AND/OR REVERSING NEW-ONSET AUTOIMMUNE DIABETES

CROSS-REFERENCE TO RELATED APPLICATIONS

The present application claims the benefit of priority of U.S. Provisional Application Ser. No. 61/046,034, which was filed Apr. 18, 2008 and U.S. Provisional Application Ser. No. 61/048,246, which was filed Apr. 28, 2008. The entire text of each of the aforementioned applications is incorporated herein by reference.

STATEMENT OF GOVERNMENT INTEREST

This invention was made with government support under Grant Number R21 DK49835-01 awarded by the National Institutes of Health (NIH). The government has certain rights in the invention.

BACKGROUND

The present disclosure generally relates to an antisense approach to prevent and/or reverse an autoimmune diabetes condition in NOD mice. This includes microsphere delivery of AS-oligonucleotides by injection to achieve therapeutic effect that causes a negative modulating activity, particularly in the non-obese-diabetic (NOD) mouse model. The microspheres are fabricated using totally aqueous conditions, which microspheres incorporate one or more antisense (AS) oligonucleotides.

Microparticles, microspheres, and microcapsules are solid or semi-solid particles having a diameter of less than one millimeter, and may be less than 100 microns, which can be formed of a variety of materials, including synthetic polymers, proteins, and polysaccharides. Microspheres have been used in many different applications, primarily separations, diagnostics, and drug delivery.

A number of different techniques can be used to make these particles from synthetic polymers, natural polymers, proteins and polysaccharides, including phase separation, solvent evaporation, emulsification, and spray drying. Generally the polymers form the supporting structure of these microspheres, and the drug of interest is incorporated into the polymer structure. Exemplary polymers used for the formation of microspheres include homopolymers and copolymers of lactic acid and glycolic acid (PLGA) as described in U.S. Pat. No. 5,213,812 to Ruiz, U.S. Pat. No. 5,417,986 to Reid et al., U.S. Pat. No. 4,530,840 to Tice et al., U.S. Pat. No. 4,897,268 to Tice et al., U.S. Pat. No. 5,075,109 to Tice et al., U.S. Pat. No. 5,102,872 to Singh et al., U.S. Pat. No. 5,384,133 to Boyes et al., U.S. Pat. No. 5,360,610 to Tice et al., and European Patent Application Publication Number 248,531 to Southern Research Institute; block copolymers such as such as Tetronic®908 and poloxamer 407 as described in U.S. Pat. No. 4,904,479 to Illum; and polyphosphazenes as described in U.S. Pat. No. 5,149,543 to Cohen et al. Microspheres produced using polymers such as these exhibit a poor loading efficiency and are often only able to incorporate a small percentage of the drug of interest into the polymer structure. Therefore, substantial quantities of these types of microspheres often must be administered to achieve a therapeutic effect. In addition, these polymers typically are hydrophobic, negatively impacting the dissolution of the drug of interest. Polymers typically used in this context include polylactic glycolic acid (PLGA).

An objective for the medical community is the delivery of nucleic acids to the cells in an animal for treatment of various diseases including diabetes. In many approaches, nucleic acids can be delivered to cells in culture (in vitro) relatively efficiently with the addition of transfection agents. In addition, in vivo, the presence of endogenous nucleases results in a high rate of nucleic acid degradation when nucleic acid is delivered to animals.

In addition to protecting nucleic acid from nuclease digestion, a nucleic acid delivery vehicle must exhibit low toxicity, must be efficiently taken up by cells and have a well-defined, readily manufactured formulation. As shown in clinical trials, viral vectors for delivery can result in a severely adverse, even fatal, immune response in vivo. In addition, this method has the potential to have mutagenic effects in vivo. Delivery by complexing nucleic acids in lipid complexes of different formulations (such as liposomes or cationic lipid complexes) can have toxic effects. Complexes of nucleic acids with various polymers or with peptides have shown inconsistent results and the toxicity of these formulations has not yet been resolved. Nucleic acids also have been encapsulated in polymer matrices for delivery, but in these cases the particles have a wide size range and the effectiveness for therapeutic applications has not yet been demonstrated. Such previous approaches can yield effects that are the opposite of a goal desired herein, including stimulation of the immune system. For example, when PLGA is incorporated into particles, the immune system is stimulated by the presence of the PLGA.

Therefore, there is a need for addressing the issues in the delivery of nucleic acids, and there is an ongoing need for development of microspheres and new methods for making microspheres. Details regarding microspheres, especially details regarding their preparation and properties, are found in U.S. Pat. Nos. 6,458,387 to Scott et al., 6,268,053, 6,090,925, 5,981,719 and 5,599,719 to Woiszwillo et al., and 5,578,709 to Woiszwillo and U.S. Patent Application Publication No. 2006/0024240 to Brown et al. These and all references identified herein are incorporated by reference hereinto.

SUMMARY OF THE INVENTION

In accordance with the present disclosure, oligonucleotides are delivered as microspheres. It is believed that such a delivery approach prevents access of the nucleases to the nucleic acids within the microsphere. Microsphere delivery of antisense (AS) oligonucleotides is carried out in order to induce dendritic cell tolerance, particularly in the NOD mouse model. The microspheres are fabricated using aqueous conditions such that antisense (AS) oligonucleotides are incorporated. These microspheres are used to inhibit gene expression and to prevent and/or reverse an autoimmune diabetes condition in NOD mice in vivo.

In a one aspect of the disclosure, three AS-oligonucleotides targeted to the CD40, CD80 and CD86 transcripts are synthesized, and an aqueous solution of the oligonucleotide mixture is prepared and combined with an aqueous polymer solution. Microspheres containing the oligonucleotides are formed, and these are delivered to the NOD mice by injection.

In one aspect of the disclosure, there is provided a method for reversing type 1 diabetes in a mammal comprising administering a microsphere composition wherein microspheres in the composition comprise oligonucleotides that are antisense to and targeted to bind to primary transcripts selected from the group consisting of CD40, CD80 and CD86 primary transcripts and combinations thereof. The oligonucleotides can be selected from the group consisting of SEQ ID NO:1, SEQ ID NO:2 or SEQ ID NO:3 and combinations thereof, or indeed any other oligonucleotides that target CD40, CD80 and CD86.

In another aspect, a method of treating or reversing type-1 diabetes in a mammal is provided comprising administering a composition comprising microspheres in an amount effective to treat or reverse type-1 diabetes, said microspheres comprising oligonucleotides that are antisense to and targeted to bind to primary transcripts selected from the group consisting of CD40, CD80 and CD86 primary transcripts, said oligonucleotides individually comprising a polynucleotide sequence selected from the group consisting of SEQ ID NO: 4, SEQ ID NO: 5 and SEQ ID NO: 6 and SEQ ID NO: 7, and modified forms of SEQ ID NO: 4, SEQ ID NO: 5 and SEQ ID NO: 6 and SEQ ID NO: 7 which target and bind CD40, CD80 and CD86 primary transcripts.

Another aspect of the disclosure is directed to a method of protecting beta cells of the pancreas of a mammal from autoimmune destruction, comprising injecting into the mammal a microsphere composition, wherein the microspheres in the composition comprise oligonucleotides that are antisense to and targeted to bind to primary transcripts selected from the group consisting of CD40, CD80 and CD86 primary transcripts and combinations thereof.

A further aspect of the invention is a process for protecting pancreatic beta cells of a mammal from autoimmune destruction, comprising administering to said mammal a composition comprising microspheres in an amount effective to protect pancreatic beta cells, said microspheres comprising oligonucleotides that are antisense to and targeted to bind to primary transcripts selected from the group consisting of CD40, CD80 and CD86 primary transcripts, and combinations thereof, said oligonucleotides individually comprising a polynucleotide sequence selected from the group consisting of SEQ ID NO: 4, SEQ ID NO: 5 and SEQ ID NO: 6 and SEQ ID NO: 7, and modified forms of SEQ ID NO: 4, SEQ ID NO: 5 and SEQ ID NO: 6 and SEQ ID NO: 7 which target and bind CD40, CD80 and CD86 primary transcripts.

Another aspect is a method of decreasing T-cell-mediated inflammation of the pancreas and/or pancreatic beta cell death in a mammal comprising administering to the mammal a microsphere composition, wherein the microspheres in the composition comprise oligonucleotides that are antisense to and targeted to bind to primary transcripts selected from the group consisting of CD40, CD80 and CD86 primary transcripts, and combinations thereof, wherein the composition is administered in an amount effective to ameliorate the symptoms of Type 1 diabetes in the mammal. In more defined aspects, the composition is administered after clinical onset of Type 1 diabetes. In alternative aspects, the composition is administered prior to clinical onset of Type 1 diabetes. In these therapeutic aspects, the administration of the composition normalizes blood glucose levels in the mammal as compared to the blood glucose levels of the mammal prior to administration.

Yet another aspect is a method of decreasing T-cell-mediated pancreatic inflammation or pancreatic beta cell death in a mammal comprising administering to said mammal a composition comprising microspheres in an amount effective to decrease T-cell-mediated pancreatic inflammation or pancreatic beta cell death, said microspheres in said composition comprising oligonucleotides that are antisense to and targeted to bind to primary transcripts selected from the group consisting of CD40, CD80 and CD86 primary transcripts, and combinations thereof, said oligonucleotides individually comprising a polynucleotide sequence selected from the group consisting of SEQ ID NO: 4, SEQ ID NO: 5 and SEQ ID NO: 6 and SEQ ID NO: 7, and modified forms of SEQ ID NO: 4, SEQ ID NO: 5 and SEQ ID NO: 6 and SEQ ID NO: 7 which target and bind CD40, CD80 and CD86 primary transcripts.

In another aspect of the invention, there is provided a method of preserving residual beta cell mass in a mammal with new-onset or preclinical autoimmune diabetes comprising administering to said mammal a composition comprising microspheres in an amount effective to preserve residual beta cell mass wherein administration of the composition maintains the beta cell mass of the mammal to at least about 15% of the mass present prior to diabetes onset, said microspheres in said composition comprising oligonucleotides that are antisense to and targeted to bind to primary transcripts selected from the group consisting of CD40, CD80 and CD86 primary transcripts and combinations thereof, said oligonucleotides individually comprising a polynucleotides sequence selected from the group consisting of SEQ ID NO: 4, SEQ ID NO: 5 and SEQ ID NO: 6 and SEQ ID NO: 7, and modified forms of SEQ ID NO: 4, SEQ ID NO: 5 and SEQ ID NO: 6 and SEQ ID NO: 7 which target and bind CD40, CD80 and CD86 primary transcripts.

The administration of the composition may regenerate the beta cell population of the mammal or halt the further deterioration of the beta cell population or both.

The composition may be administered in any form and in certain exemplary aspects is administered as an injectable form. In specific aspects, the composition is administered in combination with insulin. Where a combination therapy is used, the insulin may be administered prior to, concurrently with, or after administration of the microsphere composition.

In various embodiments, the microspheres in a composition comprise antisense oligonucleotides individually comprising the polynucleotide sequences SEQ ID NO: 4, SEQ ID NO: 5 and SEQ ID NO: 6 and SEQ ID NO: 7. In other embodiments, the microspheres in a composition comprise antisense oligonucleotides individually consisting of the polynucleotide sequences SEQ ID NO: 4, SEQ ID NO: 5 and SEQ ID NO: 6 and SEQ ID NO: 7. In further embodiments, the microspheres in a composition comprise antisense oligonucleotides having at least 80%, 85%, 90%, 95% or greater polynucleotide sequence homology to SEQ ID NO: 4, SEQ ID NO: 5 and SEQ ID NO: 6 and SEQ ID NO: 7 and which target and bind CD40, CD80 and CD86 primary transcripts.

Additional aspects are directed to methods of preserving residual beta cell mass in a subject with new-onset or preclinical autoimmune diabetes comprising administering to the subject a composition containing microspheres comprising oligonucleotides that are antisense to and targeted to bind to CD40, CD80 and CD86 primary transcripts, wherein administration of the composition maintains the beta cell mass of the mammal to at least about 15% of the mass present prior to diabetes onset. The subject may be a human subject. The subject may be a human child. The treatment method may involve repeated administration of the composition and the repeated administration increases the beta cell mass of the mammal.

In particular defined methods, 30% and as much as 70% w/w of the microspheres is oligonucleotide. Such compositions typically may comprise a ratio in the microsphere composition of antisense CD40:antisense CD80:antisense CD86 of 1:1:1.

In further embodiments, a pharmaceutical composition is provided comprising microspheres, said microspheres comprising antisense oligonucleotides individually having the polynucleotide sequences set out in SEQ ID NO: 4, SEQ ID NO: 5 and SEQ ID NO: 6 and SEQ ID NO: 7, polynucleotide sequences having at least 75% polynucleotide sequence homology to SEQ ID NO: 4, SEQ ID NO: 5 and SEQ ID NO: 6 and SEQ ID NO: 7 and which target and bind CD40, CD80 and CD86 primary transcripts, or modified forms of SEQ ID NO: 4, SEQ ID NO: 5 and SEQ ID NO: 6 and SEQ ID NO: 7 and which target and bind CD40, CD80 and CD86 primary transcripts. In some aspects of these embodiments, the microspheres comprise antisense oligonucleotides individually having at least 80%, 85%, 90%, 95% or greater polynucleotide sequence homology to SEQ ID NO: 4, SEQ ID NO: 5 and SEQ ID NO: 6 and SEQ ID NO: 7 and which target and bind CD40, CD80 and CD86 primary transcripts.

These and other aspects, objects, features and advantages of the present disclosure, including the various combinations, will be apparent from and clearly understood through a consideration of the following detailed description.

BRIEF DESCRIPTION OF THE DRAWINGS

In the course of this description, reference will be made to the attached drawings, wherein:

FIG. 2a is graph showing the size distribution of a preparation of microspheres. FIG. 2b shows a graph of the surface charge of a preparation of microspheres.

FIGS. 6a-6d are light micrographs of pancreatic tissue sections from control NOD mice stained with haemotoxylin and eosin (FIG. 6 and c; H+E) or for insulin (FIGS. 6b and 6d).

FIGS. 7a-7d are light micrographs of pancreatic tissue sections from AS-MSP treated NOD mice stained with haemotoxylin and eosin (FIGS. 7a and c; H+E) or for insulin (FIGS. 7b and 7d).

FIG. 13A shows a timeline for the experiments with mice having new-onset diabetes, and FIGS. 13B and 13C are plots of mean blood glucose levels from new-onset diabetic mice treated with either AS-MSP or controls.

FIG. 14A-C shows reversal of the type-1 diabetes phenotype in NOD mice. These figures show that upon administration of AS-MSP the blood glucose levels of the mammals return to normal within 15 days (normal levels are shown by the dashed line at approx 200 mg/dL) and remain at normal even after AS-MSP administration is stopped (day 30).

FIG. 16 depicts the uptake of oligodeoxynucleotides (ODN) by human dendritic cells (DC).

DESCRIPTION OF THE ILLUSTRATED EMBODIMENTS

Figure 1A:
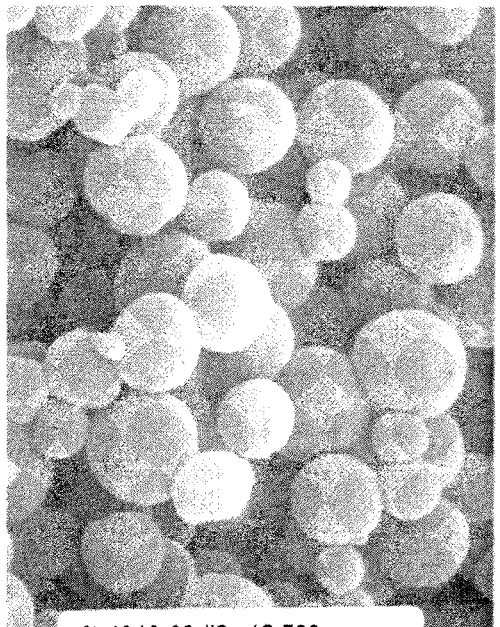
FIGS. 1a and 1b are scanning electron micrographs of microspheres of AS-oligonucleotides and poly-L-lysine polycation.

As required, detailed embodiments of the present disclosure are disclosed herein; however, it is to be understood that the disclosed embodiments are merely exemplary of the disclosure, which may be embodied in various forms. Therefore, specific details disclosed herein are not to be interpreted as limiting, but merely as a basis for the claims and as a representative basis for teaching one skilled in the art to variously employ the present disclosure in virtually any appropriate manner.

Type I diabetes is an autoimmune disorder where there is a progressive inflammation of the pancreas, and specifically, the endocrine insulin-producing beta cells. Before onset, the inflammation first renders the endocrine beta cells dysfunctional. A single injection of a microsphere formulation considerably delays disease onset in the non-obese diabetic (NOD) mouse model of human autoimmune (type 1) diabetes. Although not wishing to be bound by any particular theory, it is believed the microspheres are taken up by resident and migrating dendritic cells at the site of injection and then move into the proximal lymph nodes before onset of the disease. It is also believed that a decreased proliferation of T-cells targeted to putative beta cell antigens in vitro occurs in treated recipients. An increase may occur in the prevalence of CD4+ CD25+ putative T regulatory cells in immunodeficient NOD-scid mice reconstituted with syngeneic T-cells and dendritic cells and then administered the microspheres. Thus, a microsphere-based therapeutic composition can modulate dendritic cell activity and mobilize regulatory networks for prophylaxis.

It would be desirable to have a treatment that would prevent the onset of diabetes. It would also be desirable to have a therapeutic composition that would arrest or reverse the disease after clinical onset when a substantial number of beta cells have been destroyed. Repeated administration into new-onset diabetic mice normalizes hyperglycemia and reverses the disease. Reversal typically indicates having the individual, such as a human or other mammal, exhibit near normalization of blood glucose levels. Without being bound by any particular theory, it is believed that during "reversal", disease-induced T-cell inflammation and cell death are resisted.

One embodiment reverses autoimmune insulin-dependent diabetes by formulating and injecting antisense (AS)-oligonucleotide microspheres described herein, targeting the transcripts of CD40, CD80 and CD86. Specific examples of antisense oligonucleotides directed against the transcripts are disclosed in the Examples hereof. It will be understood that other antisense oligonucleotides may be designed to be effective in binding the CD40, CD80 and CD86 transcripts to achieve the effects described herein. It will also be understood that such oligonucleotides may incorporate modifications known in the art including, but not limited to, thioation, methylation and methoxyethylation and that the location and number of such modifications may be varied to achieve an optimal effect. These oligonucleotides are designed to induce immune tolerance that results in the reversal of the destruction of the insulin producing beta cells in the NOD mouse model.

Modified forms of oligonucleotides are also contemplated which include those having at least one modified internucleotide linkage. "Modified forms" of oligonucleotides include, without limitation, modified internucleoside linkages and/or modified bases.

In one embodiment, the oligonucleotide is all or in part a peptide nucleic acid. Other modified internucleoside linkages include at least one phosphorothioate linkage. Still other modified oligonucleotides include those comprising one or more universal bases. "Universal base" refers to molecules capable of substituting for binding to any one of A, C, G, T and U in nucleic acids by forming hydrogen bonds without significant structure destabilization.

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide".

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In still other embodiments, oligonucleotide mimetics wherein both one or more sugar and/or one or more internucleotide linkage of the nucleotide units are replaced with "non-naturally occurring" groups. The bases of the oligonucleotide are maintained for hybridization with the target polynucleotide. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

In still other embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligo consists of 2 to 4, desirably 3, groups/atoms selected from —$CH_2$—, —O—, —S—, —$NR^H$, >C=O, >C=$NR^H$, >C=S, Si$(R'')_2$—, —SO—, —$S(O)_2$—, —$P(O)_2$—, —$PO(BH_3)$—, —$P(O,S)$—, —$P(S)_2$—, —PO(R'')—, —$PO(OCH_3)$—, and —$PO(NHR^H)$, where RH is selected from hydrogen and $C_{1-4}$-alkyl, and R'' is selected from $C_{1-6}$-alkyl and phenyl. Illustrative examples of such linkages are —CH$_2$—CH$_2$—CH$_2$—, —CH$_2$—CO—CH$_2$—, —CH$_2$—CHOH—CH$_2$—, O—CH$_2$—, —O—CH$_2$—CH$_2$—, O—CH$_2$—CH= (including R$^5$ when used as a linkage to a succeeding monomer), —CH$_2$—CH$_2$—O—, —NR$^H$—CH$_2$—CH$_2$—, —CH$_2$—CH$_2$—NR$^H$, —CH$_2$—NR$^H$—CH$_2$—, —O—CH$_2$—CH$_2$—NR$^H$— NR$^H$—CO—O—, —NR$^H$—CO—NR$^H$, NR$^H$—CS—NR$^H$, NR$^H$—C(=NR$^H$)—NR$^H$, NR$^H$—CO—CH$_2$—NR$^H$—O—CO—O—, —O—CO—CH$_2$—O—, —O—CH$_2$— CO—O—, —CH$_2$—CO—NR$^H$, —O—CO—NR$^H$, —NR$^H$—CO—CH$_2$—, —O—CH$_2$—CO$_2$—NR$^H$, —O—CH$_2$—CH$_2$—NR$^H$, CH=N$^H$, CH$_2$—NR$^H$—O—, —CH$_2$—O—N= (including R$^5$ when used as a linkage to a succeeding monomer), —CH$_2$—O—NR$^H$—, —CO—NR$^H$—CH$_2$—, —CH$_2$—NR$^H$—O—, —CH$_2$—NR$^H$—CO—, —O—NR$^H$—CH$_2$—, —O—NR$^H$, —O—CH$_2$—S—, —S—CH$_2$—O—, —CH$_2$—CH$_2$—S—, —CH$_2$ CH$_2$—S—, —S—CH$_2$CH= (including R$^5$ when used as a linkage to a succeeding monomer), —S—CH$_2$—CH$_2$—, —S—CH$_2$—CH$_2$—O—, —S—CH$_2$ CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NR$^H$—, —NR$^H$—S(O)$_2$ CH$_2$—; —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(O CH$_2$CH$_3$)—O—, —O—PO(O CH$_2$CH$_2$SR)—O—, —O—PO(BH$_3$)—O—, —O—PO(NHR$^N$)—O—, —O—P(O)$_2$—NR$^H$ H—, —NR$^H$—P(O)$_2$—O—, —O—P(O,NR$^H$)—O—, —CH$_2$—P(O)$_2$—O—, —O—P(O)$_2$ CH$_2$—, and —O—Si(R")$_2$—O—; among which —CH$_2$—CO—NR$^H$—, —CH$_2$—NR$^H$—O—, —S—CH$_2$—O—, —O—P(O)$_2$—O—P(—O,S)—O—, —O—P(S)$_2$—O—, —NR$^H$ P(O)$_2$—O—, —O—P(O,NR$^H$)—O—, —O—PO (R")—O—, —O—PO(CH$_3$)—O—, and —O—PO (NHR$^N$)—O—, where RH is selected form hydrogen and C$_{1-4}$-alkyl, and R" is selected from C$_{1-6}$-alkyl and phenyl, are contemplated. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443.

Still other modified forms of oligonucleotides are described in detail in U.S. patent application No. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Other embodiments include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—CH$_2$—)$_n$ group bridging the 2' oxygen atom and the 4' carbon atom wherein n is 1 or 2. LNAs and preparation thereof are described in WO 98/39352 and WO 99/14226.

Oligonucleotides may also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, N',N'-ethano-2,6-diaminopu-rine, 5-methylcytosine (mC), 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, Nucleic Acids Research, 1997, vol. 25, pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., Angewandte Chemie, International Edition, 1991, 30, 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

In certain embodiments, the oligonucleotides of the invention are modified at one base position. In other aspects, the oligonucleotides are modified at two, three, four, five, six, seven, eight, nine, ten or more base positions. Any modification is contemplated by the invention as long as the resulting oligonucleotide retains the ability to bind to its target transcript.

Additional sequences contemplated by the present invention include, but are not limited to, those set out in Table 1.

TABLE 1

| Sequence name | Antisense sequence | SEQ ID |
|---|---|---|
| Human CD80 279-301: 5'UTR | 5' AC AAT CCA ATT GCT CAC GTA GAA 3' | 8 |
| Human CD80 274-292: 5'UTR | 5' T TGC TCA CGT AGA AGA CCC 3' | 9 |
| Human CD80 950-968 | 5' T TGG GAA ACT GGT GTG TTG 3' | 10 |
| Human CD80 1130-1152 | 5' AG ATT AAG GTA ATG GCC CAG GAT 3' | 11 |
| Mouse CD80 1007-1025 | 5' T ATT ACT GCG CCG AAT CCT 3' | 12 |
| Rat/human1 CD80 645-665 | 5' CG GTT CTT GTA CTC GGG CCA 3' | 13 |
| Rat/human2 CD80 649-667 | 5' G TCC GGT TCT TGT ACT CGG 3' | 14 |
| Human CD40 517-535 | 5' T TGG AGA AGA AGC CGA CTG 3' | 15 |
| Human CD40 792-810 | 5' C TGC ACT GAG ATG CGA CTC 3' | 16 |
| Rat/human CD40 873-891 | 5' A GAT GCG ACT CTC TTT GCC 3' | 17 |
| Human CD86 264-286 | 5' CA AAA TAC TAC TAG CTC ACT CAG 3' | 18 |
| Human CD86 277-295 | 5' T GGT CCT GCC AAA ATA CTA 3' | 19 |
| Human CD86 686-704 | 5' C AGT TCT GTG ACA TTA TCT 3' | 20 |

Type 1 diabetes is manifested by the autoimmune destruction of the pancreatic insulin-producing beta cells in the NOD mouse, as well as in humans. At the time of clinical onset, humans typically have 10-20% or less of residual beta cell mass. Sparing of any of this residual mass can result in remaining insulin levels which are adequate to regulate glucose levels. In addition, reversing the destruction of beta cells may result in the partial regeneration of the beta cell population. The oligonucleotide-containing microparticles of the present disclosure are provided to interfere with the autoimmune destruction of the beta cells.

It will be appreciated that dendritic cells (DC) can be activated to be potent antigen-presenting cells found in all tissues and which are present under the skin. These antigen-presenting dendritic cells function as triggers of the immune response, including autoimmune responses, through the activation of T-cells, particularly in lymph nodes. Although not wishing to be bound by theory, CD40, CD80 and CD86 are believed to be important for the autoimmune response, and the downregulation of these molecules is thought to promote autoimmune hyporesponsiveness. In addition, certain cytokines, such as interferons and interleukins, are reduced as a result of the hyporesponsiveness.

In making the microspheres that are used for treatment of autoimmune diabetes in mice, one, two or three AS-oligonucleotides may be dissolved in aqueous solution and combined with water soluble polymer(s) and a polycation. The solution typically is incubated at about 60-70° C., cooled to about 23° C., and the excess polymer is removed.

The nucleic acids typically comprise between about 30 and about 100 weight percent of the microspheres and have an average particle size of not greater than about 50 microns, typically not greater than about 20 microns, and can be not more than about 10 microns. Typically, they are prepared as follows. An aqueous solution of the oligonucleotide or oligonucleotides is prepared. When microspheres containing three oligonucleotides are to be prepared, aliquots from three oligonucleotide solutions are combined. Each solution contains one of these three oligonucleotide types. The final solution containing oligonucleotides typically contains about 10 mg/ml of oligonucleotide.

In specific examples, the microsphere formulation contains 65%, 70%, 75%, 80%, 85%, 90% w/w or greater load of oligonucleotides. In such embodiments, the compositions have a poly-L-lysine content of 6-10% w/w, in addition the moisture content of the microspheres varies and can be approximately 4%. The oligonucleotides are present, in one aspect, in a ratio of 1:1:1 of antisense CD40:antisense CD80:antisense CD86. Additional formulations contemplated by the invention will comprise putative autoantigens. These can include, but are not limited to intact human insulin, glutamic acid decarboxylase (GAD) and Insulinoma-Associated protein-2 (IA-2).

These are combined with aliquots of a 10 mg/ml stock solution of polycation. Examples of polycations are poly-lysine and poly-ornithine. Others include polyethyleneimine (PEI), prolamine, protamine, polyvinyl pyrrolidone (PVP), polyarginine, vinylamine, and derivatives of positively-charged polysaccharides, such as positively charged chitosan, and combinations thereof. The polycation solution can be at volumetric ratios of polycation:oligonucleotide of from about 1:1 to about 4:1. Commonly used polycations include poly-L-lysine.HBr (up to 70,000 Daltons available from Bachem) and poly-L-ornithine.HBr (e.g. 11,900 Daltons available from Sigma).

Polymer solutions also are prepared. These can function as phase-separation enhancing agents. Examples of suitable polymers include linear or branched polymers, copolymers and block copolymers. These polymers can be water soluble, semi-water soluble, water-miscible, or soluble in a water-miscible solvent. Examples of polymers include pharmaceutically acceptable additives such as polyethylene glycol (PEG) of various molecular weights, such as PEG 200, PEG 300, PEG 3350, PEG 8000, PEG 10000, PEG 20000, etc. and poloxamers of various molecular weights such as poloxamer 188 and Pluronic F127 or Pluronic F68. A commonly used polymer is polyvinylpyrrolidone (PVP). Another polymer is hydroxyethylstarch. Other amphiphilic polymers can also be used alone or in combinations. The phase-separation enhancing agent can also be a non-polymer such as a mixture of propylene glycol and ethanol.

In a typical embodiment, a polymer solution of polyvinyl pyrrolidone and/or of polyethylene glycol may be prepared and combined with the other solutions. Heating, cooling, centrifuging and washing multiple times provide an aqueous suspension which typically is frozen and lyophilized to form a dry powder of microspheres comprising oligonucleotide and polycation.

The microspheres are suitable for in vivo delivery by an injectable route, including intravenous, intramuscular, subcutaneous, intraperitoneal, intrathecal, epidural, intra-arterial, intra-articular and the like. Other delivery routes that can be practiced include such as topical, oral, rectal, nasal, pulmonary, vaginal, buccal, sublingual, transdermal, transmucosal, optic or intraocular. Advantageous for the purposes of this disclosure is the syringable delivery route. Thus, in one aspect, the microparticles or microspheres can be aspirated into a syringe and injected through fine needles. A suitable delivery route is injection with a fine bore needle, which includes subcutaneous, ocular and the like. The term "fine bore needle" means needles of at least 20 Gauge size, typically between about 22 Gauge and about 30 Gauge and above. In one aspect, the fine bore needle is least as fine as 24 Gauge, at least as fine bore as 26 gauge, and at least as fine as 28 Gauge.

In one aspect, the microparticles or microspheres are capable of being injected at a concentration of at least but not limited to about 10 µg of oligonucleotide per ml of the composition being injected. For example, from about 150 to about 500 mg of oligonucleotide are injectable in a delivery volume of not more than about 1 ml, and generally less than about 2 ml for many applications. The dosage can be divided into two or three or more doses over the day or given in a single daily dose.

In various aspects, the microparticles or microspheres are capable of being injected at a concentration of at least but not limited to about 0.01 to about 1000 mg per ml of the composition being injected. In further aspects, the microparticles or microspheres are capable of being injected at a concentration of at least about 0.02, 0.03. 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 25, 30, 35, 40, 45, or 50 mg per ml or more of the composition being injected. In related aspects, the microparticles or microspheres are capable of being injected at a concentration of at least about 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 mg per ml of the composition being injected.

Injection delivery is made during a normal injection time period. Typically such time periods are, without limitation, not more than about 20 seconds or less.

Without being bound by any particular theory, it is believed that microspheres containing the antisense oligonucleotides exemplified herein down-regulate cell surface molecules CD40, CD80 and CD86. The microspheres are injected and dendritic cells are believed to actively uptake the oligonucleotide microspheres. These oligonucleotides suppress the expression of cell surface cell molecules CD40, CD80 and CD86 in dendritic cells. The administration of these antisense oligonucleotide microspheres after development in the NOD mouse effectively reverses diabetes.

The following Examples illustrate certain features and advantages of the disclosure in order to further illustrate the disclosure. The Examples are not to be considered limiting or otherwise restrictive of the disclosure.

EXAMPLES

Example 1

Three AS-oligonucleotides targeted to the CD40, CD80 and CD86 primary transcripts were synthesized. The AS-oligonucleotide sequences used in this Example are, with asterisks indicating sites of thioation in the backbone:

```
Seq ID 1: CD40-AS: 5'C*AC* AG*C C*GA* GG*C* AA*A
                   GA*C* AC*C A*T*G C*AG* GG*C*
                   A-3'

Seq ID 2: CD80-AS: 5'-G*GG* AA*A G*CC* AG*G A*AT*
                   CT*A G*AG* CC*A A*TG G*A-3'

Seq ID 3: CD86-AS: 5'-T*GG* GT*G C*TT* CC*G T*AA*
                   GT*T C*TG* GA*A C*AC* G*T*C_3'
```

An aqueous solution of the oligonucleotide mixture was prepared by combining aliquots of three oligonucleotide solutions, each of which contained one type of oligonucleotide, to form a 10 mg/ml solution of the three types of oligonucleotides. A 10 mg/ml solution of poly-L-lysine.HBr in deionized water (poly-L-lysine.HBr up to 70,000 Daltons, by Bachem, King of Prussia, Pa.) was prepared. The poly-L-lysine.HBr was added to the oligonucleotides solution at a volumetric ratio of 1:1. The mixture was vortexed gently. A 25% polymer solution containing 12.5% PVP (polyvinyl pyrrolidone, 40,000 Daltons, Spectrum Chemicals, Gardena, Calif.) and 12.5% PEG (polyethylene glycol, 3,350 Daltons, Spectrum Chemicals, Gardena, Calif.) in 1M Sodium Acetate (Spectrum, Gardena, Calif.) at pH5.5 was added in a 2:1 volumetric ratio as follows: 0.75 ml of AS-oligonucleotides, 0.75 ml of poly-L-lysine.HBr, 3.0 ml of PEG/PVP, and a total volume of 4.50 ml.

The batch was incubated for 30 minutes at 70° C. and then cooled to 23° C. Upon cooling, the solution became turbid and microspheres were formed. The suspension was then centrifuged, and the excess PEG/PVP was removed. The resulting pellet was washed by resuspending the pellet in deionized water, followed by centrifugation and removal of the supernatant. The washing process was repeated three times. The aqueous suspension was frozen and lyophilized to form a dry powder of microspheres comprising oligonucleotide and poly-L-lysine.

Figure 1B:
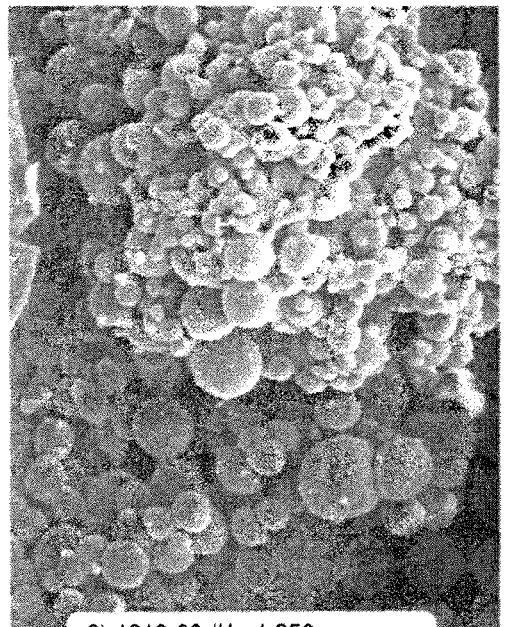
Figure 2A:
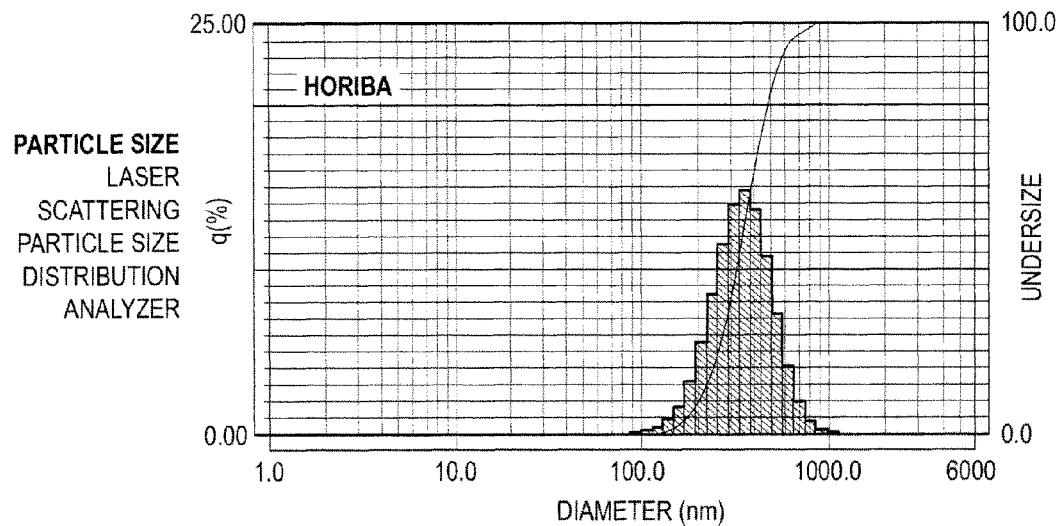
FIGS. 2a and 2b are graphs showing the properties of a microsphere preparation according to the disclosure.
Figure 2B:
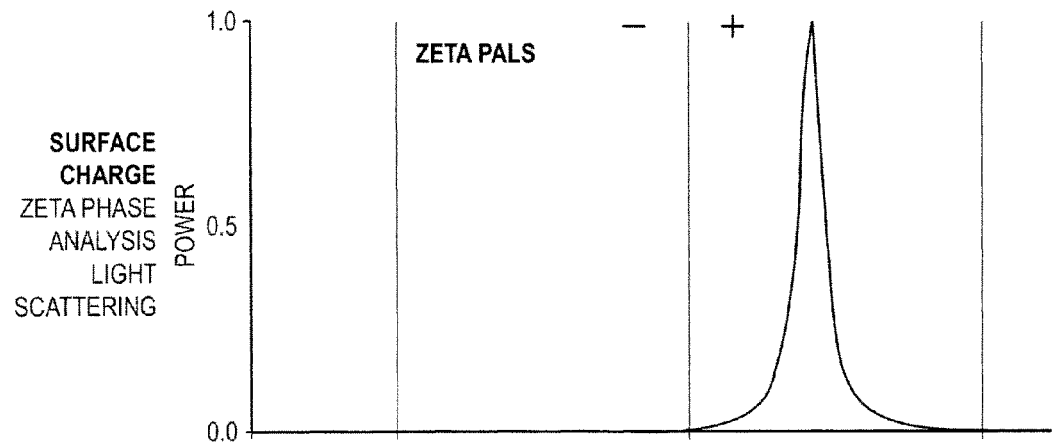
Figure 3:
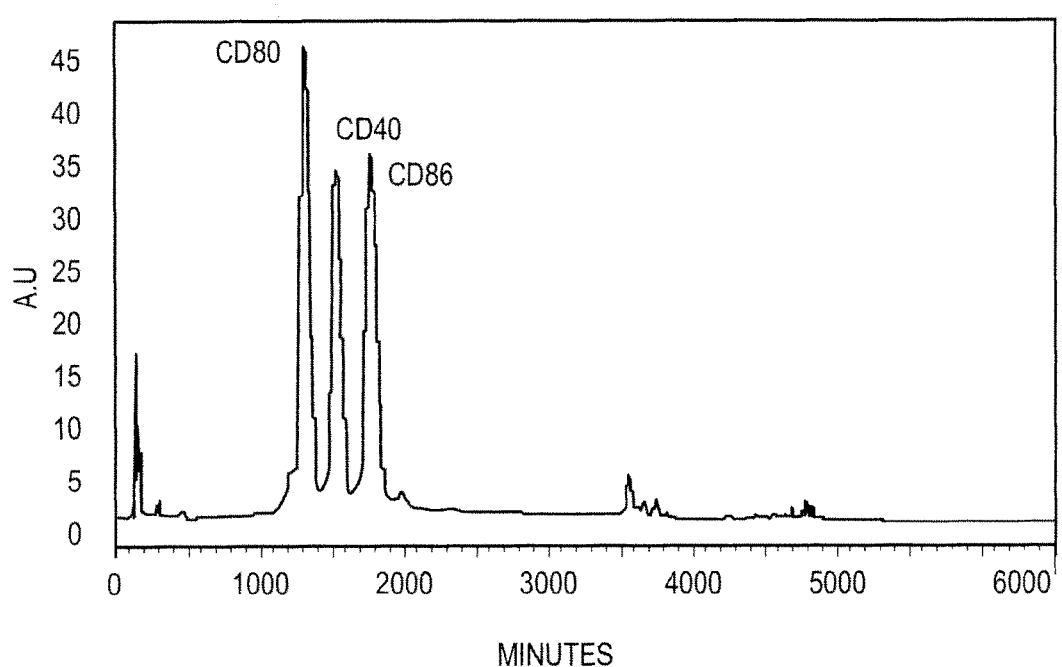
FIG. 3 is a RP-HPLC chromatogram of the oligonucleotides after deformulation of microspheres.

FIG. 1 a and b present representative scanning electron micrographs (SEM) of 1:1 poly-L-lysine:oligonucleotide ratio microspheres at two different magnifications. Microspheres, 0.5-4 μm in size, with an average particle size of approximately 2.5 μm were fabricated. FIG. 2a shows the size distribution of one preparation of microspheres made according to the disclosure as revealed by laser light scattering. FIG. 2b shows the determination of the surface charge of a microsphere preparation (Zeta potential) by light scattering. FIG. 3 shows a reverse phase (RP) HPLC method used to quantitate the loading and assess the integrity of the antisense oligonucleotide components of the microspheres after deformulation. Microspheres were formulated using CD86, CD40, CD80 oligonucleotides and poly-L-lysine (PLL; MW 30-70 kD). The microspheres were then deformulated using competitive displacement of the DNA oligonucleotides from the PLL by poly-L-aspartic acid (PAA). PAA was selected as a polyamino acid reagent that does not absorb at 260 nm and does not interfere with quantification of oligonucleotides at 260 nm. In RP-HPLC profiles such as FIG. 3, the area under each peak is proportional to amount of each oligonucleotide loaded into the microsphere. As shown in FIG. 3, the peak heights indicate approximately equal loading of each oligonucleotide into microspheres. The loading of oligonucleotides into microspheres was calculated to be from about 65% to about 80% by weight. FIG. 3 also shows that the integrity of the oligonucleotides was not affected by the microsphere formulation process, as indicated by the narrow distribution of the peaks after deformulation.

Example 2

Figure 4:
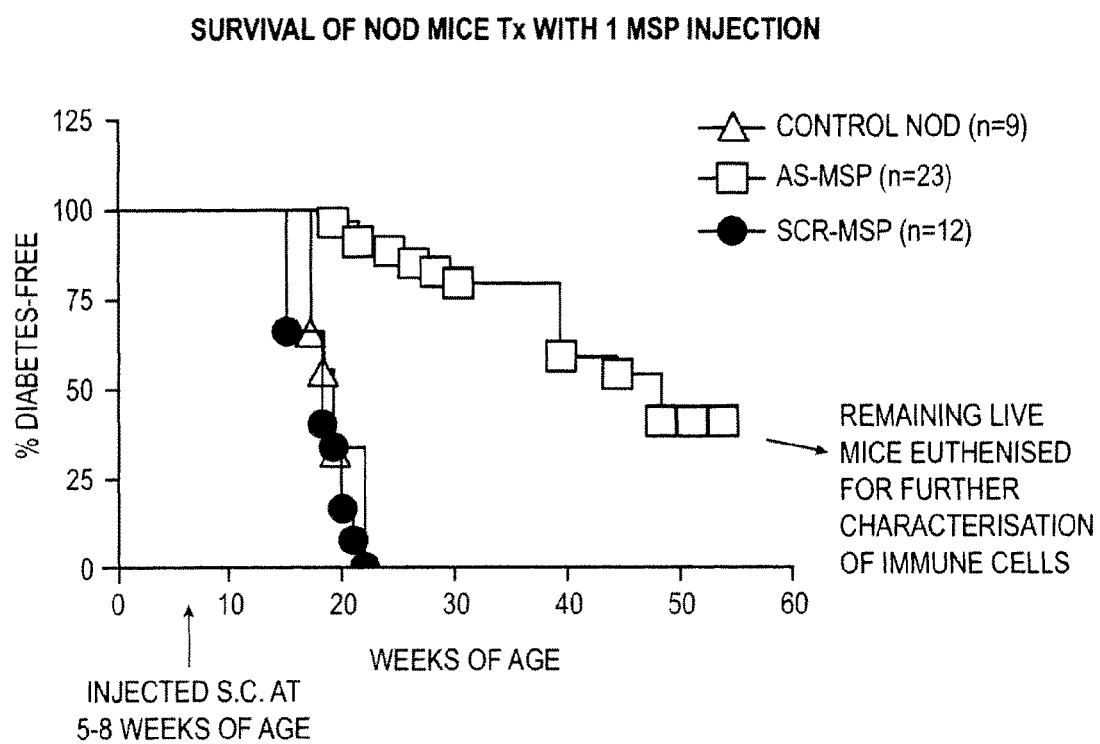
FIG. 4 is a plot showing the prevention of diabetes in NOD mice treated multiple times with antisense oligonucleotide microspheres (AS-MSP) of the disclosure compared to animals treated with scrambled oligonucleotides microspheres or with the PBS vehicle alone.

In this Example, the results of tests that cover prevention aspects of the disclosure are shown. As shown in FIG. 4, a single AS-MSP administration into NOD mice at 5-8 weeks of age delays diabetes onset. Two groups of NOD female mice (5-8 weeks old) were given a single subcutaneous injection of antisense-oligonucleotides formulated into microspheres of the disclosure (AS-MSP). The formulation was injected in injected in an amount considered to contain 50 μg of a 1:1:1 mixture of each antisense oligonucleotide (anti-CD40, anti-CD80 and anti-CD86). Other groups of mice were injected with scrambled sequence microspheres (SCR-MSP) or PBS vehicle (control NOD). Blood glucose was measured weekly via tail vein puncture. Diabetes was confirmed after two consecutive readings of >280-300 mg/dL. FIG. 4 shows the cumulative survival of two independently-treated cohorts.

Figure 5:
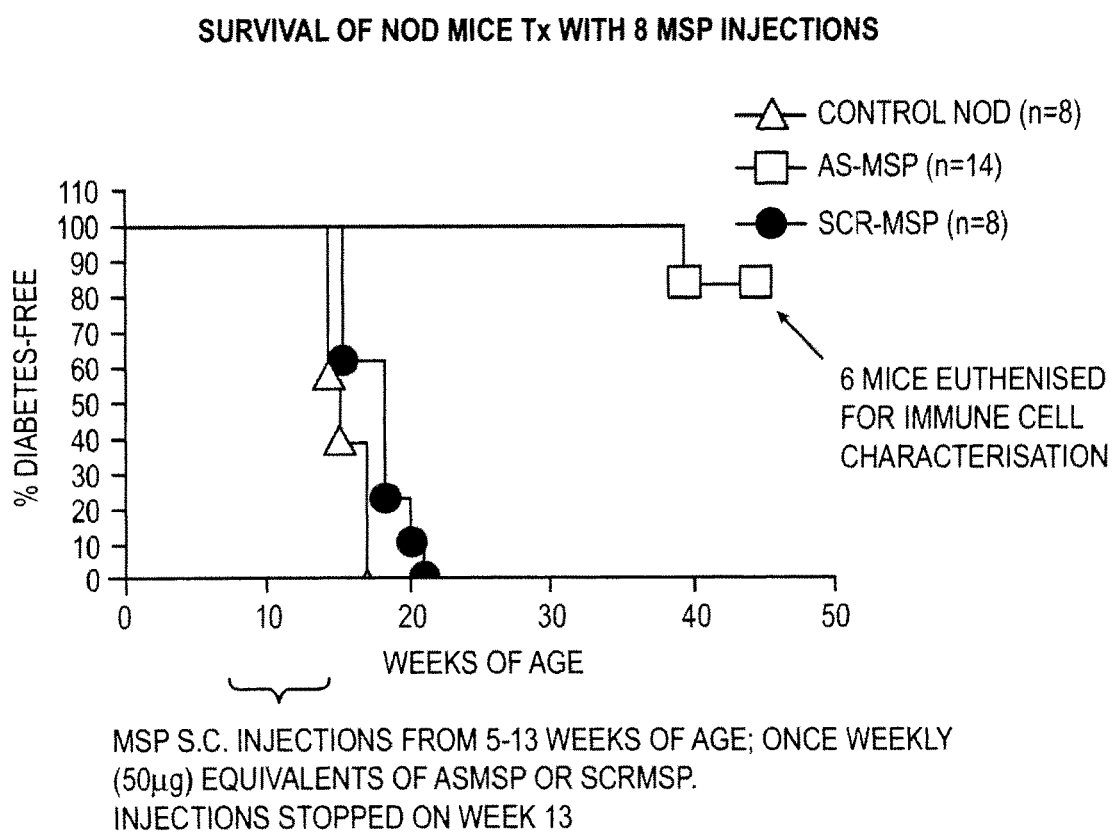
FIG. 5 is a plot showing the prevention of diabetes in NOD mice treated once with AS-MSP of the disclosure compared to animals treated with scrambled oligonucleotide microspheres or with the PBS vehicle alone.

FIG. 5 shows that multiple AS-MSP administration into NOD mice at 5-8 weeks of age prevents diabetes onset. NOD female mice (5-8 weeks old) were given eight consecutive single subcutaneous injections (once weekly) of antisense oligonucleotide formulated into microspheres according to the disclosure. Injections (50 μg of a 1:1:1 mixture of each antisense oligonucleotides or scrambled oligonucleotides) were given once weekly for eight weeks and stopped at week 13. Other groups of mice were injected with scrambled sequence microspheres (SCR-MSP) or PBS vehicle (control NOD). FIG. 5 shows the cumulative survival of treated animals.

FIGS. 6a and 6b show sections of pancreatic tissue from mice that received no treatment and thus progress spontaneously to autoimmunity (diabetic NOD mice) stained with haemotoxylin and eosin (H+E; FIG. 6a) or stained for insulin (FIG. 6b). FIGS. 6c and 6d show sections of pancreatic tissue from mice treated with SCR-MSP formulations (injections started in parallel with the groups treated with specific AS-MSP). These sections were also stained with haemotoxylin and eosin (H+E; FIG. 6c) or stained for insulin (FIG. 6d). The SCR-MSP mice all developed diabetes.

FIGS. 7a and 7b shows sections of pancreatic tissue from mice treated when less than 8 weeks of age (prevention model) and treated with the antisense microspheres of the disclosure stained with haemotoxylin and eosin (H+E; FIG. 7a) or stained for insulin (FIG. 7b).

Figure 8A:
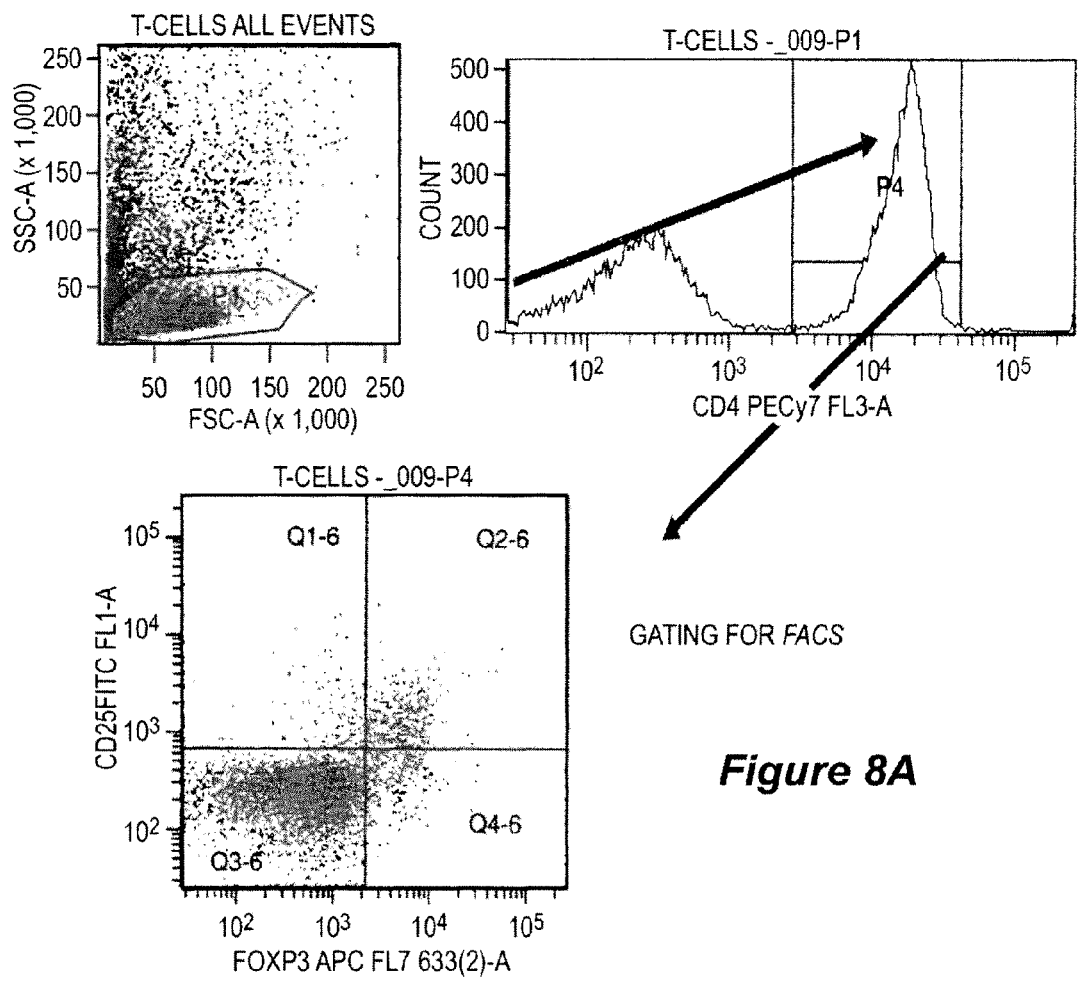
FIG. 8 shows a FACS analysis of T cells obtained from mice treated with the AS-MSP of the disclosure or from control animals.
Figure 8B:
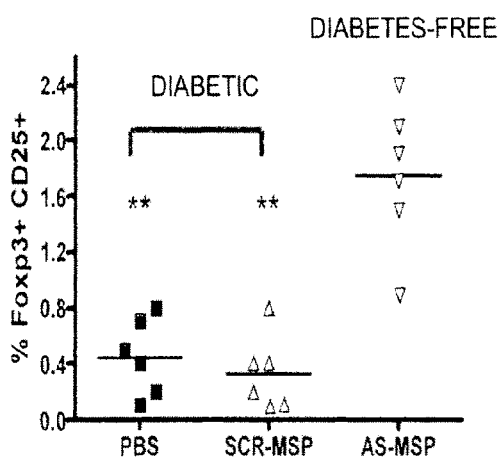
Figure 8C:
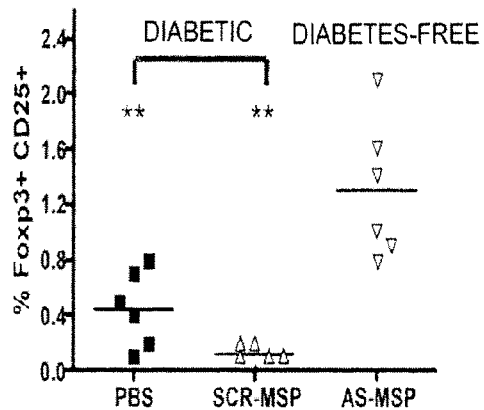

As shown in FIG. 8, T-cells from AS-MSP treated, NOD mice exhibit increased prevalence of Foxp3+CD25+putative $T_{reg}$ cells. FIG. 8A shows the gating used for FACS analysis. FIG. 8B shows percentages of Foxp3+CD25+ T-cells that were enriched from the spleen and FIG. 8C the percentages from the pooled lymph nodes for ASMSP-treated diabetes-free mice selected at random from the ASMSP diabetes-free cohort or from or from animals treated with scrambled sequence microspheres (SCR-MSP) or treated with PBS vehicle.

Figure 9A:
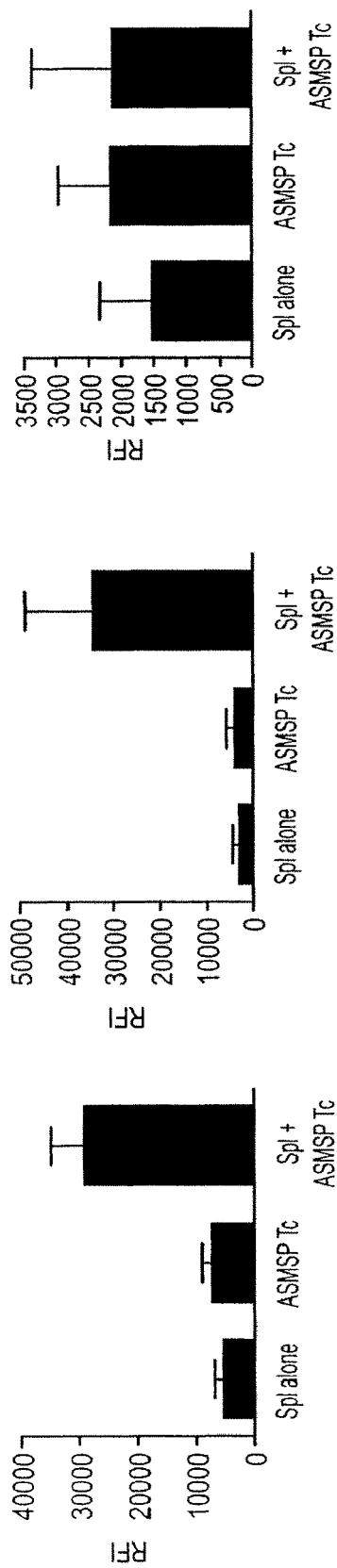
FIG. 9 shows plots of relative fluorescent intensity (RFI) demonstrating the proliferation of T cells from animals treated with AS-MSP and cultured with splenocytes according to the disclosure.
Figure 9B:
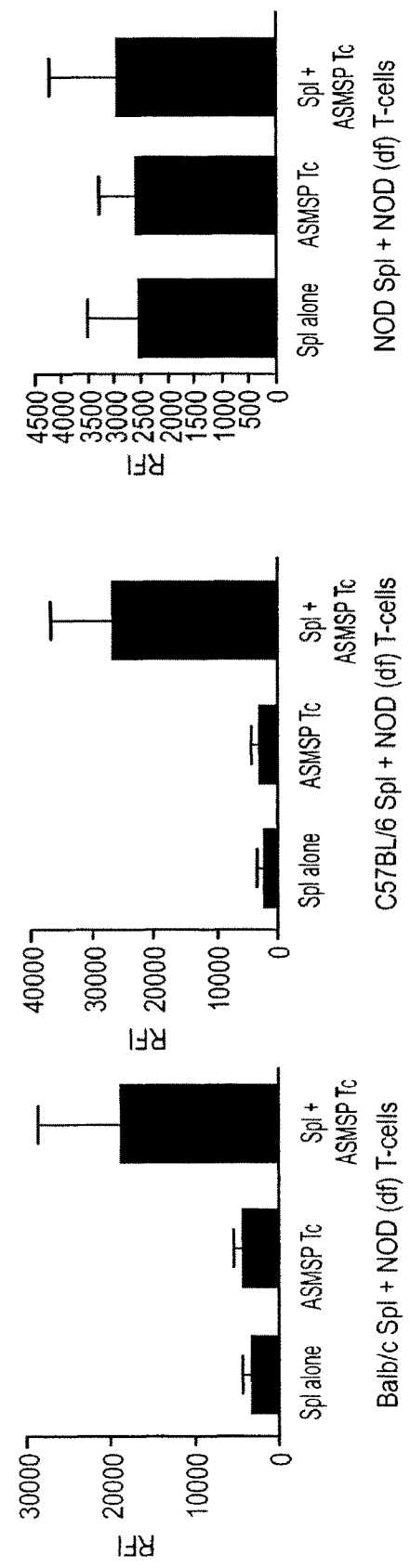

FIG. 9 shows that T-cells from ASMSP-treated diabetes-free NOD mice proliferate when co-cultured with allogeneic splenocytes. T-cells from diabetes-free NOD mice treated with ASMSP were obtained over enrichment columns and co-cultured with γ-irradiated splenocytes from Balb/c, C57BL6 or syngeneic diabetes-free NOD mice (10 weeks of age). Proliferation was measured four days later using the Cyquant reagent. Spl refers to allogeneic irradiated splenocytes.

Figure 10A:
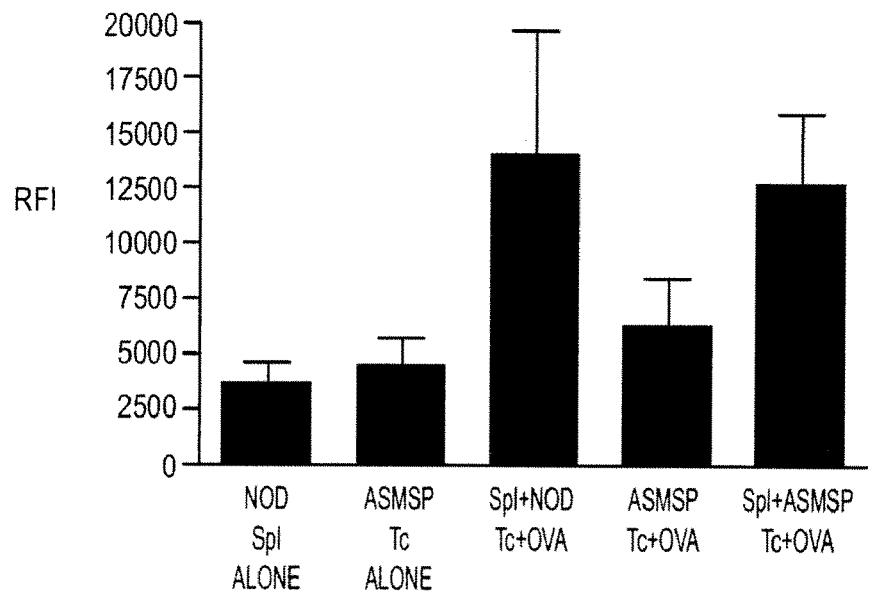
FIG. 10 shows plots of RFI demonstrating the proliferation of T-cells from AS-MSP treated, diabetes-free NOD mice in the presence of syngeneic irradiated splenocytes and ovalbumin in vitro.
Figure 10B:
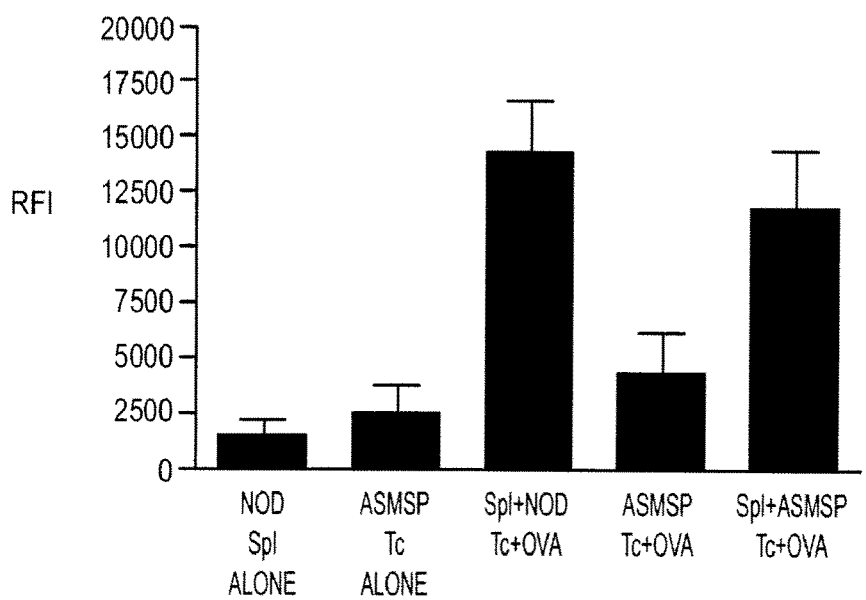

As shown in FIG. 10, T-cells from ASMSP-treated, diabetes-free NOD mice proliferate in the presence of syngeneic irradiated splenocytes and ovalbumin in vitro. T-cells were enriched from the spleen or the pooled lymph nodes of ASMSP-treated diabetes-free mice selected at random from the ASMSP diabetes-free cohort.

Figure 11A:
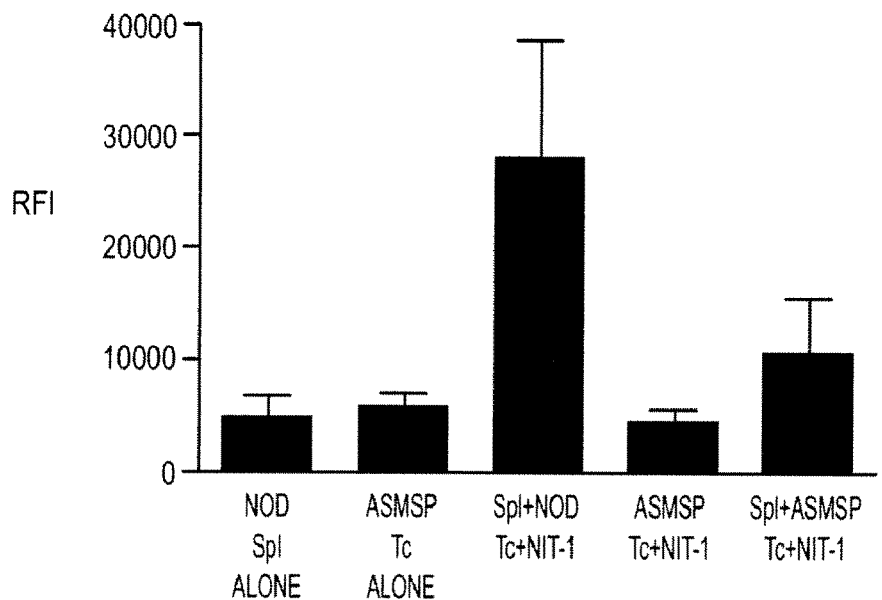
FIG. 11 shows plots of RFI demonstrating the suppressed proliferation of T-cells from AS-MSP-treated, diabetes-free NOD mice in the presence of syngeneic islet lysate in vitro.
Figure 11B:
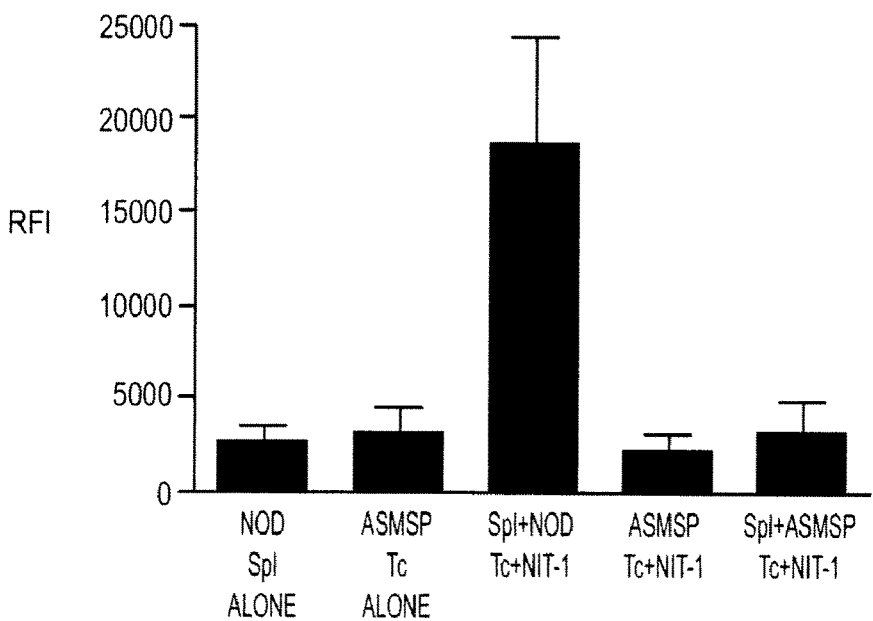

FIG. 11 shows that T-cells from ASMSP-treated, diabetes-free NOD mice exhibit suppressed proliferation in the presence of syngeneic islet lysate in vitro. T-cells were enriched from the spleen or the pooled lymph nodes of ASMSP-treated diabetes-free mice selected at random from the ASMSP diabetes-free cohort as described in FIG. 4. Irradiated NOD splenocytes (from diabetes-free 10 week-old NOD mice) were used as antigen-presenting cells and parallel cultures were pulsed with NIT-1 lysate (1 μg/well)(or PBS vehicle).

A major concern for eventual translation of diabetes-suppressive therapies into human trials is the antigen specificity (and therefore the cell specificity) of the treatment approach and whether the treatment confers global and non-specific suppression. To address these issues, randomly-selected diabetes-free mice were euthanised from the cohorts shown in FIG. 4 to ascertain the proliferation of splenic and lymph node T-cells to alloantigen, nominal antigen (in the form of intact ovalbumin) and to syngeneic beta cell-derived antigen in the form of cell lysate from the NOD derived insulinoma cell line NIT-1. While insulin and glutamic acid decarboxylase (GAD) are viable candidate autoantigens with mechanistic and teleologic involvement, the nature of the initiating autoantigen remains unclear. Nevertheless, it is reasonable to consider that it should be beta-cell resident. Therefore, the NIT-1 cell line which derives from an NOD insulinoma was used as a source of beta cell antigen in cocultures of T-cells from diabetes-free NOD mice treated with the AS-MSP to determine the possibility of antigen-specific hyporesponsiveness. From these studies, it was seen that T-cell proliferation to nominal and alloantigen is maintained whereas there is T-cell hypoproliferation in cocultures with NIT-1 cell lysate.

Furthermore, ascertaining the cytokine profile in the co-culture supernatants, we observed a significant decrease in TNFα production by T-cells from AS-MSP-treated, diabetes-free NOD mice even in the presence of NIT-1 lysate. Although IFNγ production was slightly decreased in the co-cultures of T-cells from the AS-MSP-treated mice, it was not statistically-distinguishable from the co-cultures with T-cells from PBS-treated mice in the presence of NIT-1 lysate. The assay, finally, could not detect the presence of IL-4, IL-10 or TGFβ in the supernatants.

Example 3

Figure 12A:
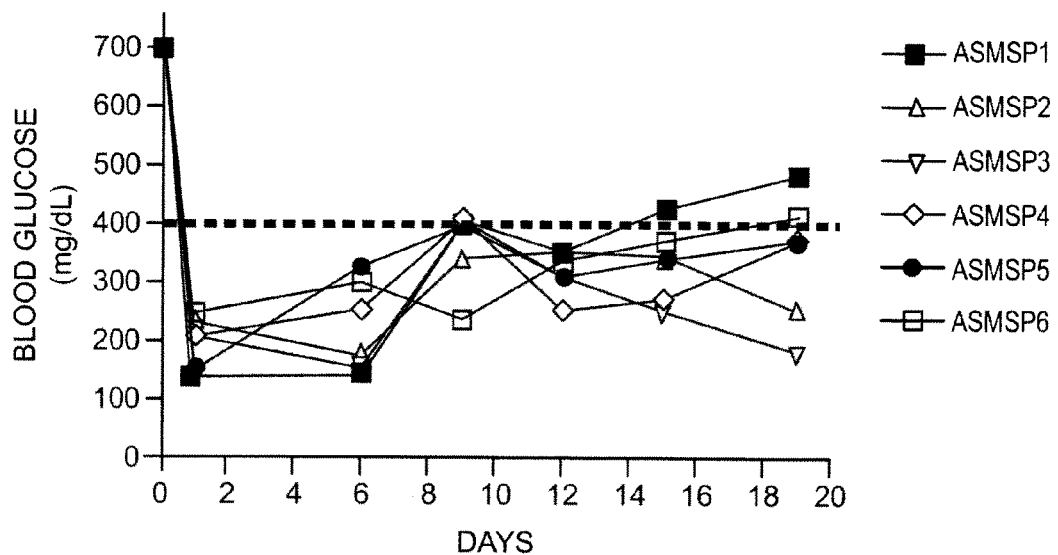
FIG. 12 is a plot of blood glucose levels from new-onset diabetic mice treated with either microspheres containing antisense or scrambled oligonucleotides.
Figure 12B:
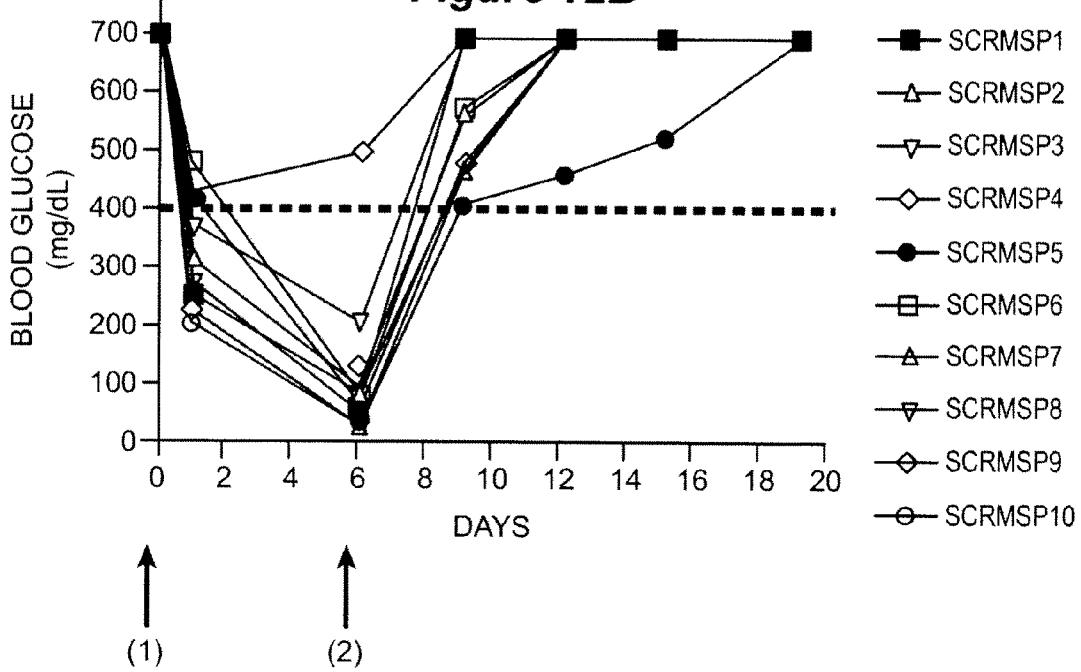

The ability of antisense oligonucleotide microspheres to reverse the symptoms of diabetes in early onset NOD mice was also tested. A timeline for these experiments is shown in FIG. 13A. NOD mice that had early onset were selected by testing blood glucose levels and identifying animals that had a blood glucose level greater than 400 mg/dL. The selected animals were given insulin pellets to normalize blood glucose levels to below 300 mg/dL. The insulin was withdrawn and a series of parenteral injections of microspheres was started. Six animals were injected twice weekly with microspheres containing the CD40, CD80 and CD86 antisense oligonucleotides. A further ten animals were injected with microspheres containing a mixture of oligonucleotides with scrambled sequences that are not directed against CD40, CD80 and/or CD86. Each injection for both groups of animals contained 50 μg of oligonucleotides in microspheres in 100 microliters of injection solution. Two of the animals in the scrambled group were euthanized before the end of the experiment due to poor physical condition. After the commencement of the injection protocol, blood glucose levels were sampled twice weekly. The animals were non-fasting during the experiment. The results are plotted in FIG. 12, wherein the indicator (1) signifies insulin pellet installation and indicator (2) signifies insulin pellet removal and initiation of MSP injections twice weekly. It is noted that the maximum blood glucose value reported in FIG. 12 is 700 mg/dL, which corresponds to the maximum reading of the meter used, it being understood that a 700 mg/dL data point indicates a blood glucose reading of 700 mg/dL or higher. All animals in the group that received the microspheres containing the mixture of CD40, CD80, CD86 antisense oligonucleotides (ASMSP1 through ASMSP6) showed significantly lower glucose levels than the animals that received the microspheres with scrambled oligonucleotides (SCRMSP1 through SCRMSP10). Furthermore, four of six animals in this ASMSP group showed a blood glucose level below 400 mg/dL, typically considered to be a threshold indicator of diabetes onset.

In FIG. 13A, the timeline for the experiments is shown. The mean non-fasting blood glucose (FIG. 13B) and the mean fasting blood glucose levels for each group are plotted (FIG. 13C) (+/−SEM). In some mice, ASMSP administration was withdrawn as shown in FIG. 13A. As shown in FIGS. 13B and 13C, multiple rounds of AS-MSP administration into new-onset diabetic NOD female mice improves blood glucose levels and result in stable fasting euglycemia even after AS-MSP withdrawal relative to untreated animals (control), animals treated with PBS or animals treated with scrambled oligonucleotides (SCR-MSP) microspheres.

FIGS. 7c and 7d show sections of pancreatic tissue from NOD mice that were treated with antisense formulations after onset of diabetes and showed reversal of the disease. The sections are stained with haemotoxylin and eosin (H+E; FIG. 7c) or stained for insulin (FIG. 7d).

Three different AS-oligonucleotides can be incorporated into microspheres according to methods disclosed herein and such microspheres can be used as a composition to prevent and/or reverse new onset autoimmune diabetes via immuno-regulatory dendritic cell induction. Indeed, a single injection of the composition delayed disease onset and repeated administration into new-onset diabetic mice normalized hyperglycemia, suggesting reversal of disease. In these studies, insulin was administered daily until blood glucose fell below 300 mg/dL. Insulin then was stopped whereupon AS-MSP were administered subcutaneously. In an exemplary dosing regiment, the animals were administered 2 mg AS-MP per kg body weight two times a week for 3-4 weeks. The diabetes-free NOD mice were monitored.

Figure 14A:
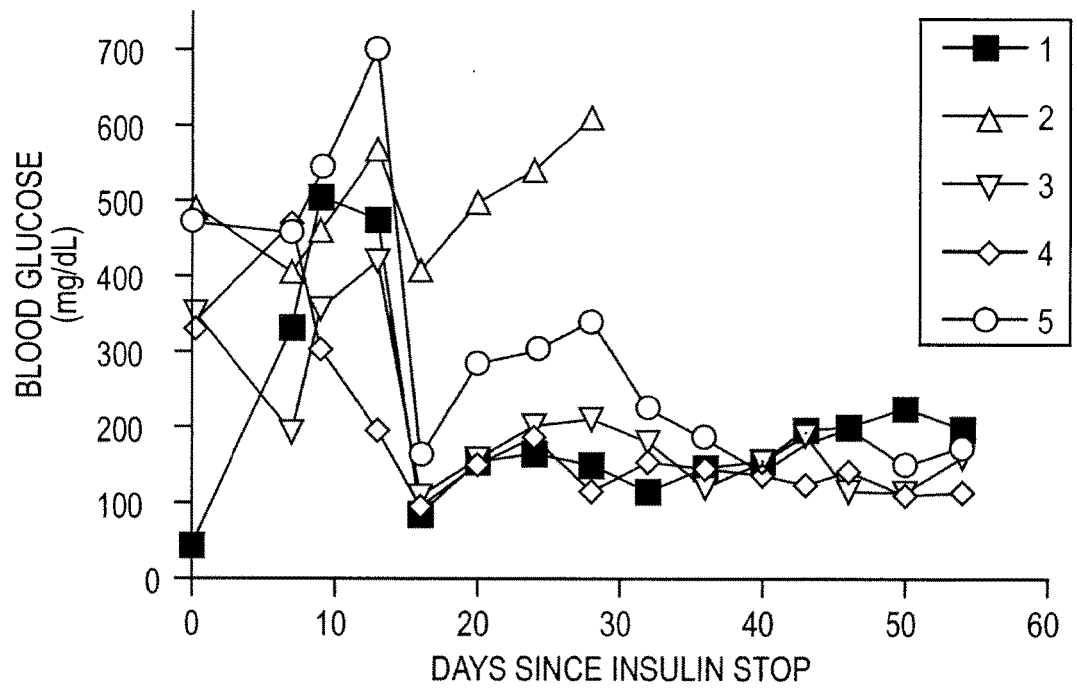
Figure 14B:
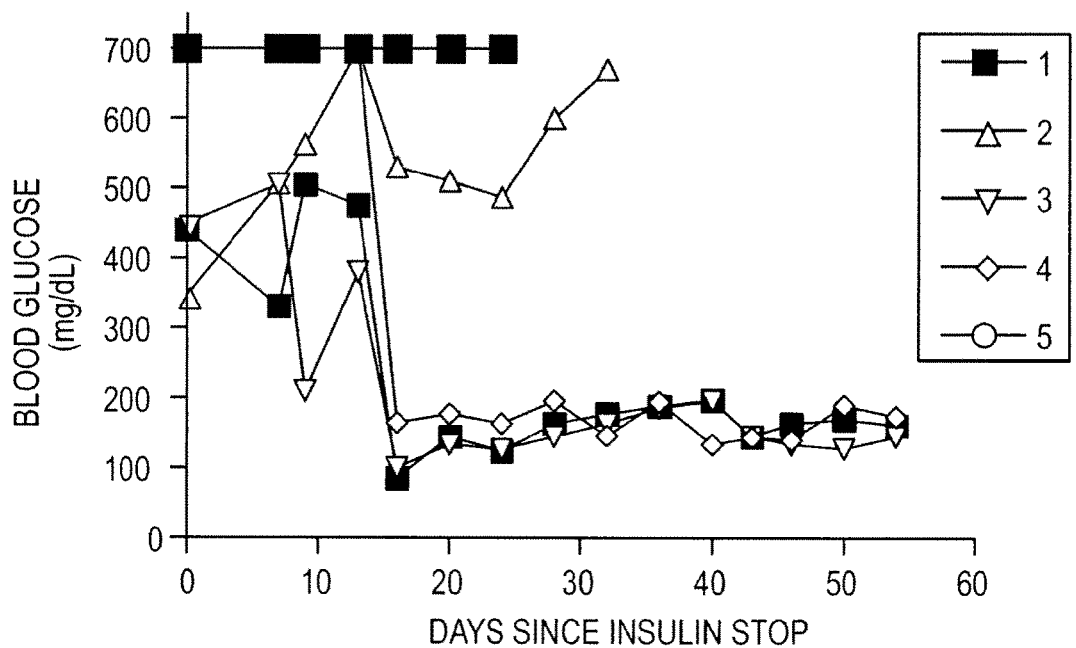

In FIG. 14A-C it is demonstrated that administration of AS-MSP to NOD mice returns the blood glucose levels of said mice to normal levels and the normalization of said blood glucose level is maintained for an extended period of time. As shown in FIGS. 14B and 14C, AS-MSP was administered between days 0-30 after insulin administration was stopped. The blood glucose level returned to normal by day 15 post insulin stop and remained at a normal level until the end of the monitoring period (day 55).

Figure 15:
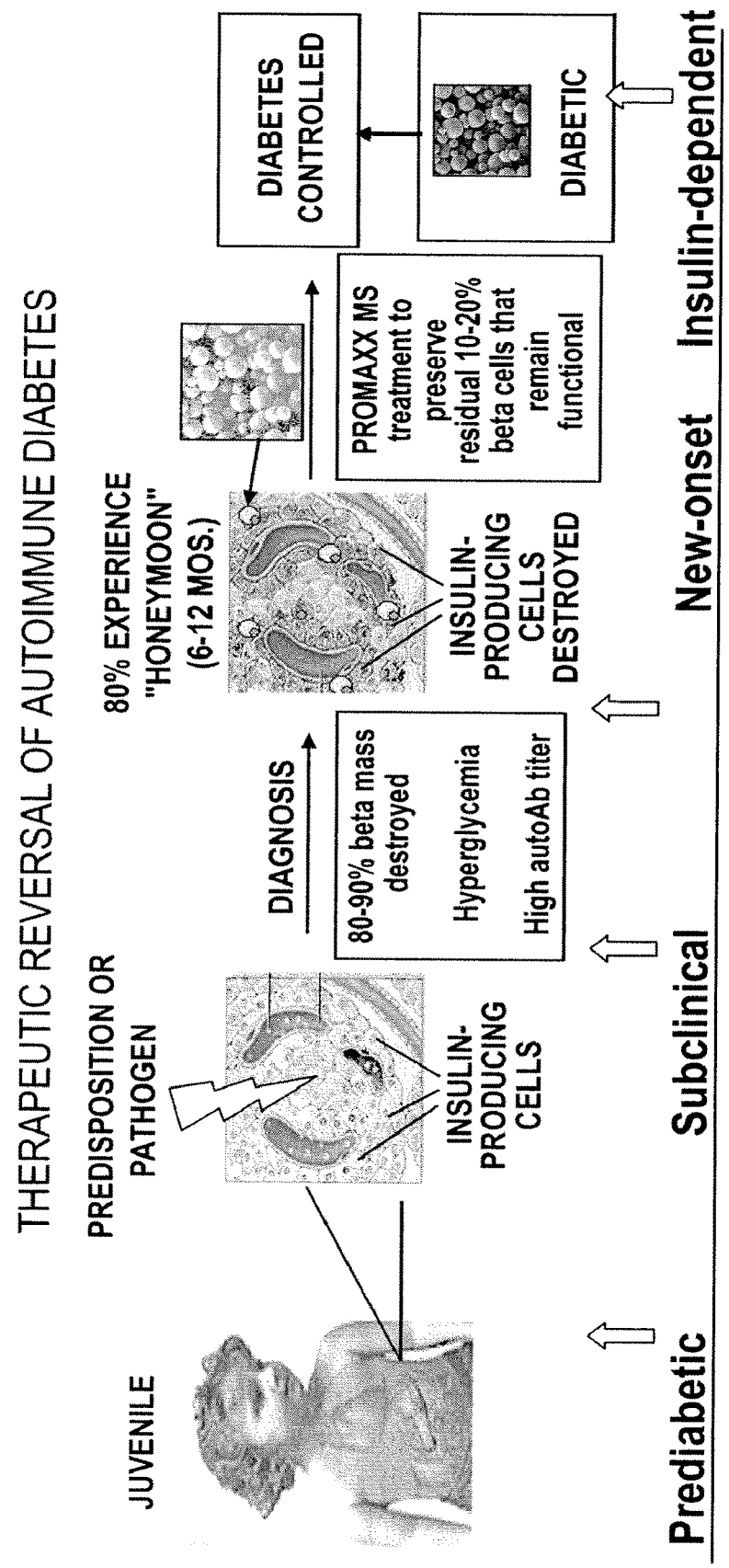
FIG. 15 Model depicting therapeutic reversal of autoimmune diabetes.

A diagram showing the impact of therapeutic reversal of autoimmune diabetes is show in FIG. 15. If microsphere treatment were administered at the new onset "honeymoon" shown in FIG. 15, it is predicted that there would be a preservation of the 10-20% beta cells that remain functional, thereby leading to a control of the diabetes and reducing the dependence of the patient on insulin.

It will be understood that the embodiments of the present disclosure which have been described are illustrative of some of the applications of the principles of the present disclosure. Numerous modifications may be made by those skilled in the art without departing from the true spirit and scope of the disclosure. Various features which are described herein can be used in any combination and are not limited to precise combinations which are specifically outlined herein.

Example 4

The following human antisense sequences were used in the studies described below:

```
                                            (SEQ ID NO: 4)
h-CD40 AS:  5' ACT GGG CGC CCG AGC GAG GCC TCT GCT
            GAC 3'

(SEQ ID NO: 5)
h-CD80 AS:  5' TTG CTC ACG TAG AAG ACC CTC CCA GTG
            ATG 3'

(SEQ ID NO: 6)
h-CD86 AS:  5' AAG GAG TAT TTG CGA GCT CCC CGT ACC
            TCC 3'

(SEQ ID NO: 7)
NH-CD80 AS: 5' TTG CTC ACG TAG AAG ACC CTC CAG TGA
            TG 3'
```

Human DC were obtained from peripheral blood via Ficoll-Hypaque centrifugation of blood, separation of adherent from non-adherent cells on plates with subsequent propagation of the adherent cells in GM-CSF/IL-4 in AIM V medium (Thornton et al., 2000, J Immunol 164:183-190; Thornton et al., 1998, J Exp Med 188:287-296; Medarova et al., 2005, Diabetes 54:1780-1788; Petrovsky et al., 2003, Cancer Res 63:1936-1942; Gmyr et al., 2001, Cell Transplant 10:109-121) and used for all experiments outlined below. T-cells were enriched from the non-adherent cells harvested during the DC propagation following selection on CD3 columns. All cells were obtained from healthy volunteers.

Figure 16A:
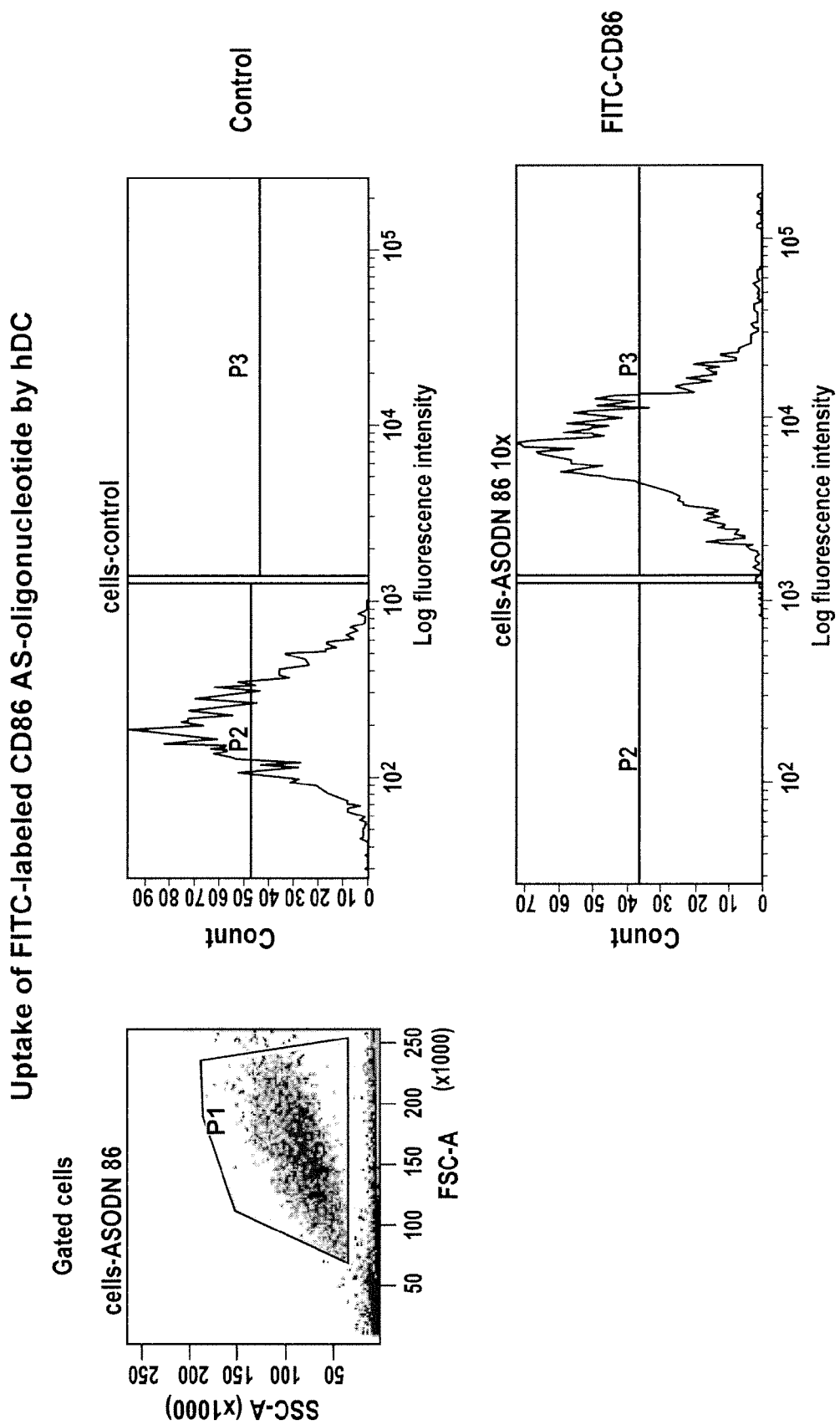
FIG. 16A shows the uptake of FITC-labeled CD86 AS-oligonucleotide by hDC.
Figure 16B:
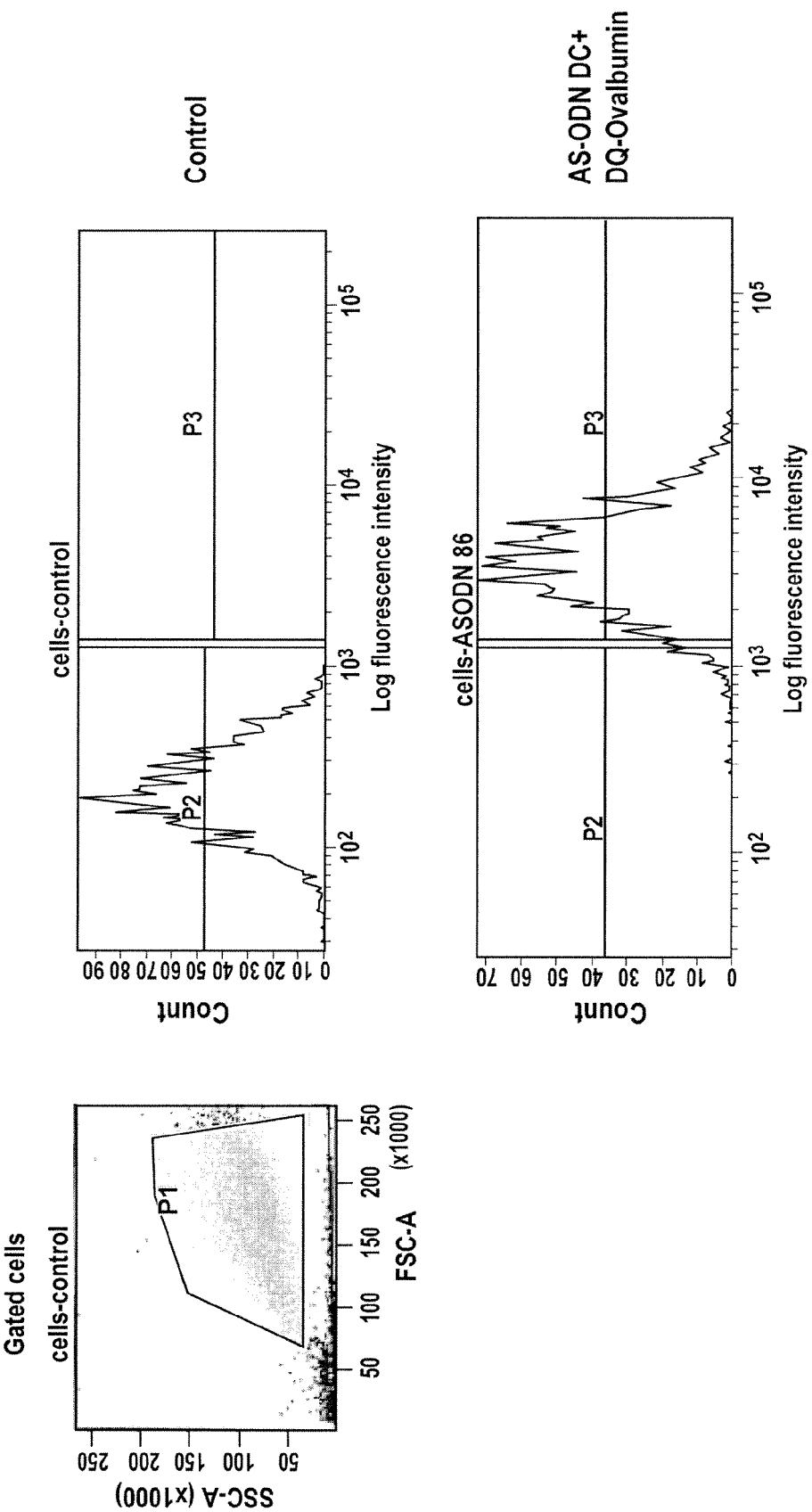
FIG. 16B shows the uptake/processing of DQ-Ovalbumin by AS-ODN-treated hDC.
Figure 16C:
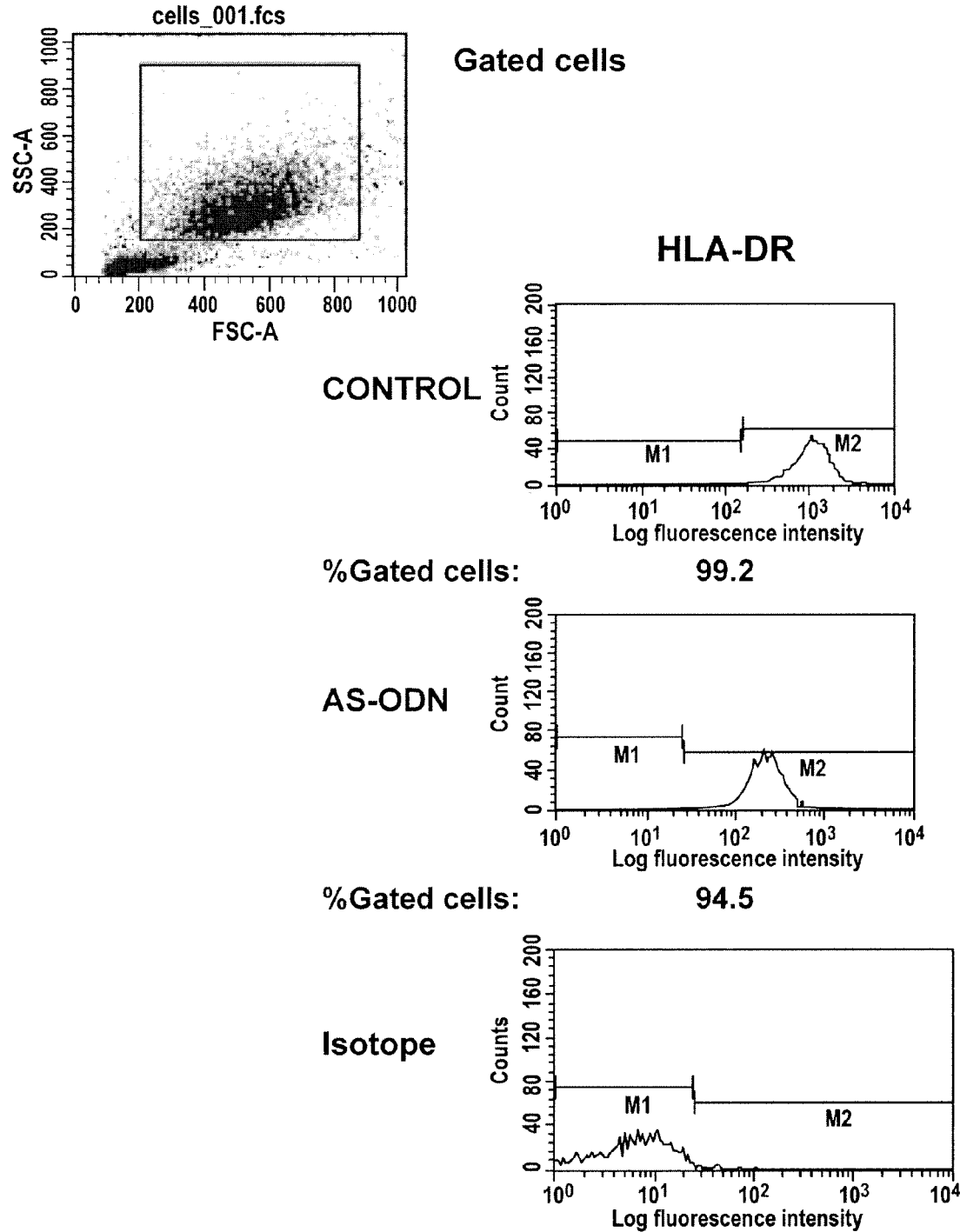
FIG. 16C shows the phenotype by FACS of DC embodiments following LPS treatment.

Uptake Of ODN By Human DC: Human DC rapidly (by five hours) take up fluorescent NF-kappaB and AS-ODN without altering cell viability and function as assessed by PI/Annexin V staining, cell surface CD86, CD80, CD40 and class II MHC expression and uptake/processing of DQOvalbumin™. FIG. 16A shows the uptake of FITC-labeled CD86 antisense oligonucleotide by human DC by 24 hours following addition to the medium (3.3 µM final). DC immaturity is associated with their capacity for phagocytosis of exogenously-supplied particles and endosomal/lysosomal processing. FIG. 16B demonstrates that AS-ODN DC were capable of taking up exogenously supplied protein (DQ-Ovalbumin) and more importantly, their fluorescence indicates that the antigen was processed within endocytic compartments (intact DQ-ovalbumin does not fluoresce, but processed does). At the same time, the AS-ODN-treated DC (mixture of all three antisense oligonucleotides) displayed dramatically-suppressed CD86 and CD80 cell surface levels without any changes in ICAM-1 or class I and class II HLA-important for antigen presentation even with lipopolysaccharide (LPS) stimulation; a treatment that dramatically augments the cell surface levels of CD80 and CD86. $1 \times 10^5$ human DC were first treated with the AS-ODN mixture (3.3 µM final of each oligonucleotide) for a period of 24 hours and then treated with LPS (10 µg/mL) or PBS vehicle for an additional 24 hours. The cells were then stained with the fluorescent antibodies indicated or isotype controls. FACS analyses were then carried out (FIG. 16C).

Figure 17:
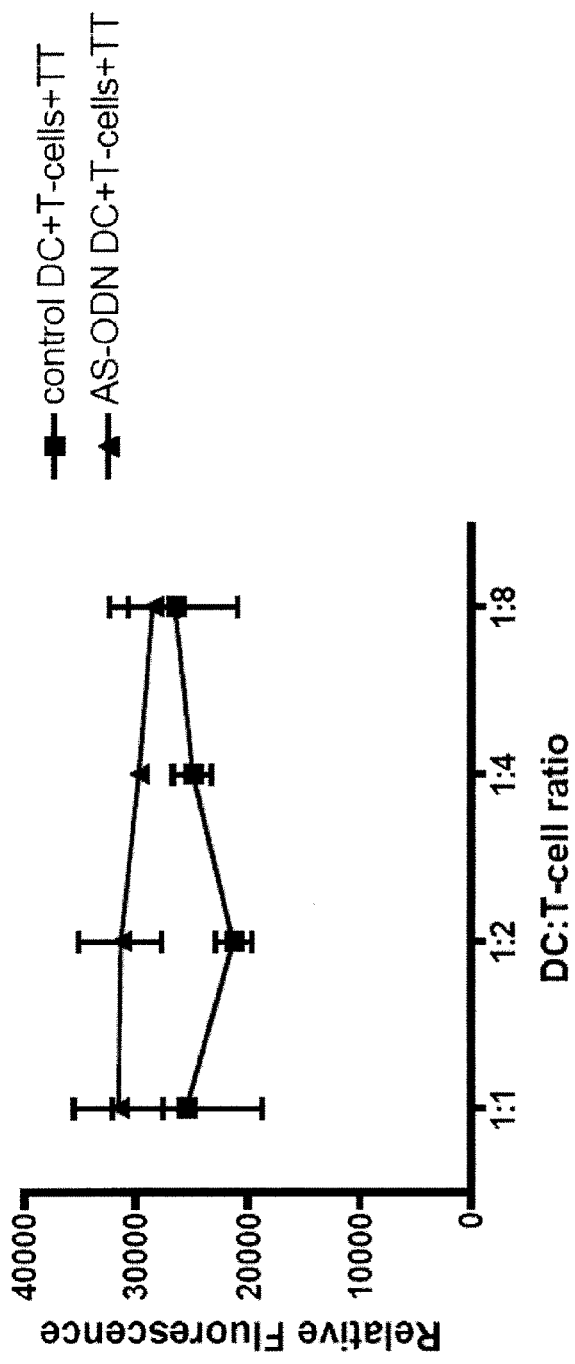
FIG. 17 depicts the proliferation of T-cells from a healthy human volunteer, recently administered a tetanus booster vaccine, co-cultured with autologous AS-ODN-treated peripheral blood-derived DC in the presence of tetanus toxoid. Error bars indicate the standard error of the mean of the response from three independent co-cultures of cells of the same individual.
Figure 18:
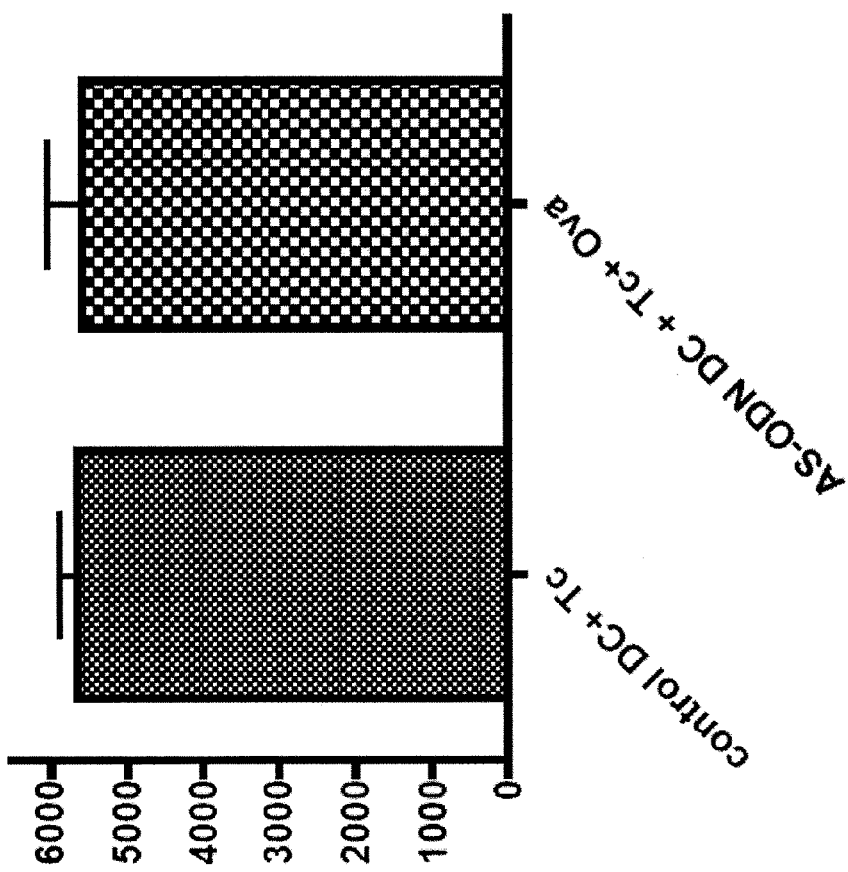
FIG. 18 shows the proliferation of T-cells from healthy human volunteers co-cultured with autologous AS-ODN-treated peripheral blood-derived DC in the presence or absence of intact ovalbumin as nominal antigen. Error bars indicate the standard error of the mean of the response from three independent volunteers.

Responses to vaccination and nominal antigen: Human PBMC-derived dendritic cells treated with AS-ODN (SEQ ID NOs 4, 6 and 7) exhibited normal activation of syngeneic T-cells and in syngeneic T-cells in co-culture with tetanus toxoid (where the T-cells were obtained from recently-vaccinated individuals); FIG. 17. Additionally, AS-ODN DC stimulated normal T-cell responses when the DC were pulsed with ovalbumin, a nominal antigen FIG. 18. In both assays, comparisons were made to co-cultures with untreated DC as stimulators. Co-cultures were established where the 1:1 ratio of DC:T-cells consisted of $1 \times 10^4$ cells. Proliferation was measured by the CyQuant reagent on day 5 of co-culture. Exogenous antigen (tetanus toxoid or intact ovalbumin were provided at a final concentration of 5 µg/mL for the duration of the co-culture period.

Figure 19:
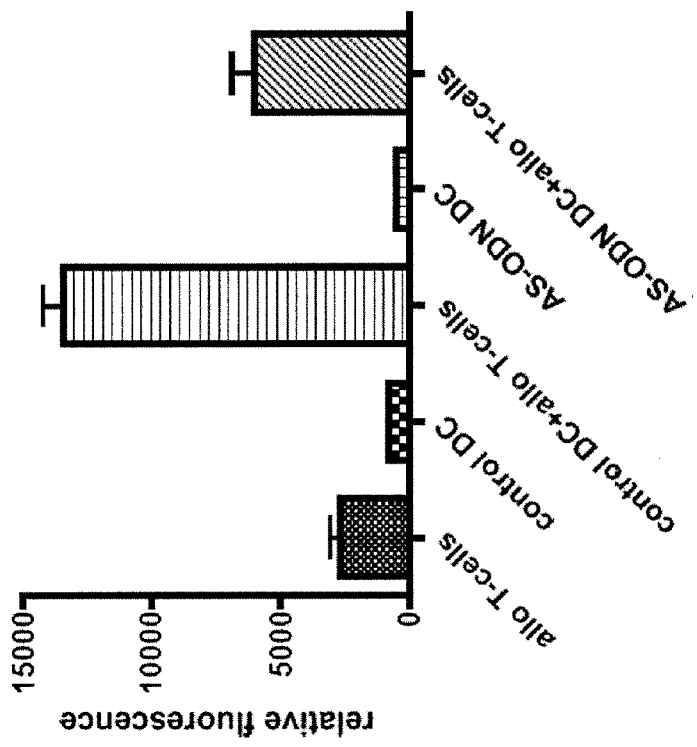
FIG. 19 depicts the proliferation of T-cells from healthy human volunteers co-cultured with allogeneic AS-ODN-treated peripheral blood-derived DC or untreated allogeneic DC. Error bars indicate the standard error of the mean of the response from three independent volunteers where the DC donor remained the same.

Responses To Alloantigen: In FIG. 19, AS-ODN DC are shown to have provided weaker proliferation stimuli to allogeneic T-cells in culture. The T-cell proliferation in co-cultures with AS-ODN DC was lower compared to co-cultures with control DC as stimulators. Co-cultures were established where the 1:1 ratio of DC:Tcells consisted of $1 \times 10^4$ cells. Proliferation was measured by the CyQuant reagent on day 5 of co-culture.

Detailed DC Phenotype Evaluation In Vitro In As-ODN Treated DC: Tables 2 and 3 (below) demonstrate the effects of CD40, CD80 and CD86 antisense ODN-prepared DC on prevention of LPS-stimulated DC maturation (upregulation of co-stimulation proteins) in samples from two healthy volunteers measured by FACS.

Leukocytes were obtained from two healthy volunteers and used to generate either control DC or AS-ODN DC (from each of the two volunteers). Then, the DC were activated to maturation with LPS (lipopolysaccharide) to see if there was upregulation of CD40, CD80, CD86 by FACS analysis. In the control DC, LPS stimulated CD40, CD80, CD86 upregulation at the surface, but was unable to in the AS-ODN DC. This confirms that the AS-ODN suppress the expression of CD40, CD80, CD86 even in the presence of a powerful maturation signal (LPS) which normally upregulates their expression on the surface. Data is provided in Tables 2 and 3.

TABLE 2

| Condition | CD Marker | % Positive cells (M1) |
|---|---|---|
| Control-No Oligos or LPS | CD86 | 56.50 |
| Control-No Oligos or LPS | CD80 | 8.50 |
| Control-No Oligos or LPS | CD40 | 5.10 |
| LPS Only | CD86 | 59.20 |
| LPS Only | CD80 | 37.10 |
| LPS Only | CD40 | 20.50 |
| Oligos + LPS | CD86 | 34.80 |
| Oligos + LPS | CD80 | 14.80 |
| Oligos + LPS | CD40 | 5.50 |

TABLE 3

| Condition | CD Marker | % Positive cells (M1) |
|---|---|---|
| Control-No Oligos or LPS | CD86 | 59.90 |
| Control-No Oligos or LPS | CD80 | 18.60 |
| Control-No Oligos or LPS | CD40 | 7.00 |
| LPS Only | CD86 | 63.00 |
| LPS Only | CD80 | 51.50 |
| LPS Only | CD40 | 33.10 |
| Oligos + LPS | CD86 | 48.90 |
| Oligos + LPS | CD80 | 33.10 |
| Oligos + LPS | CD40 | 11.40 |

Example 5

Microspheres Comprising Sequences (as Described in Example 4) of Antisense Oligonucleotides Complementary to Human CD40, CD80 and CD86 Costimulatory Molecules were Fabricated as Follows Approximately 6.0 mg of poly-L-lysine in aqueous solution was heated to 70° C. in a water bath into a 15 ml conical tube. 6.9 mg of a mixture of CD40, CD80 and CD86 antisense oligonucleotides (SEQ ID NOs. 4, 6 and 7 as described in Example 4) in aqueous solution was heated to 70° C. in a water bath into a 15 ml conical tube. A 12.5%—PEG/12.5% PVP solution was also heated to 70° C. in a water bath. The poly-L-lysine was pipetted into the antisense oligonucleotides solution. The resulting suspension was mixed by briefly swirling with the pipette tip. Next, the tube was quickly returned to 70° C. water bath and incubated for 5 minutes. The PEG/PVP solution was then added to the ASO/PLL solution. This was mixed briefly by swirling with the pipette tip.

The tube was then quickly returned to 70° C. water bath and incubated for 5 to 10 minutes. Next, the formulation was cooled to 4° C. using at a rate of 1° C./minute cooling. The samples were then water washed on ice.

The samples were then centrifuged at 4750 rpm for 10-30 minutes at 4° C. The supernatant was then removed and the microspheres were resuspended with an equal volume of $H_2O$ at 4° C. The microspheres were then washed 3 additional times by centrifugation, washing and resuspension at 4750 rpm for 5-10 minutes at 4° C. by removing the supernatant, resuspending the microspheres and resuspending with an equal volume of $H_2O$ at 4° C.

After the fourth centrifugation step, the microspheres are resuspended to a concentration of approximately 10 mg per ml. The samples were then frozen on dry ice or in a −80° C. freezer for 30 minutes. Finally, the samples were lyophilized to dryness over approximately a 24 hour period.

Example 6

A Gram Scale Batch Produced for Animal Toxicology Studies as Follows

Microsphere (MS) Formulation: A typical production process for the antisense oligonucleotide microspheres (ASO MS) is described below using antisense (SEQ ID NOs. 4, 6 and 7) as described in Example 4. A 10 g quantity of antisense oligonucleotide (ASO) production batch was produced using three 2 L production aliquots at 2.3 mg/ml of starting ASO (13.8 g).

| Total reaction Volume (ml) | ASO conc. (mg/ml) | PLL conc. (mg/ml) | Cooling rate (bath) | Polymer/ASO incubation time (min) | PEG and PVP conc. (% each) |
|---|---|---|---|---|---|
| 2000 mL | 2.3 | 2 | 0.9 C/min | 10 | 8.33 |

The 2 L batch utilized a 3 L open Stainless Steel(SS) vessel. The poly-1-lysine (PLL) solution and nuclease-free water was added to a sterile 1000 ml bottle and heated to 70° C. The ASO cocktail was added to a sterile 250 ml bottle and heated to 70° C. The PEG/PVP solution was added to the 3 L vessel and heated to 70° C. The ASO cocktail was added to the hot PLL/water mixture and form an ASO/PLL complex. The complex will be held at 70° C. for five minutes and then was added to the 3 L vessel containing the PEG/PVP while stirring with a sterile flat-blade lifter. The solution was held for 10 minutes at 70° C. The entire formulation was cooled from 70° C. to 2° C. at a rate of ~0.9° C./min. The suspension was transferred for polymer removal and washing.

Polymer Removal/Washing: All open manipulations were performed in a laminar flow hood. The ASO-MS suspension was transferred into four 500 mL pre-sterilized polypropylene conical bottles. The bottles were centrifuged at 3700 rpm (3200 g force) for 30 min at 4° C. The supernatant was poured off and pre-cooled (4° C.) 0.2 µm filtered USP water was added back to the bottles (the same volume as supernatant removed). The pellets were resuspended by shaking the bottles manually and using cold-water sonication. This process was repeated 3 more times, with the centrifugation time at 10 min instead of 60 min. The final resuspension was done in ~500 mL of filtered USP Water and the total volume was added to a lyophilization pan.

Lyophilization: Final drying to a dry powder was accomplished by lyophilization. ASO-MS were bulk lyophilized in sanitized 10"×16" stainless steel pans (1 per batch). All 3 batches were frozen at −40° C. on the shelf of the SP Industries (FTS) Freeze Dryer FD-165. The batches were then added back to the freeze dryer and lyophilized over three days. The cycle used included a freezing step at −40° C. for 4 hours, primary drying step at −10° C. for 48.5 hours, a slow ramp to a secondary drying step of 20° C. for 2 hours, a slow ramp to a hold step at −5° C., then a slow ramp to final hold step of 20° C. At this point, the freeze dryer was backfilled with 0.2 µm filtered cleanroom air and the trays transferred to a laminar flow hood for harvest.

Harvest/Packaging: ASO-MS were harvested into a 100 mL autoclaved glass bottle and cap. A total of 24 aliquots were sampled into 10 mL or 20 mL autoclaved glass vials and caps (based upon dose load) for the dose ranging study. Additional material was sampled for analytical testing, bioburden, endotoxin, and other applications. All harvesting and sampling were performed in a laminar flow hood using pre-sterilized or sanitized components.

Resuspension Vehicle Preparation: Glycine powder was dissolved in USP Water. The ASO-MS will designed to be resuspended in the vehicle at the time of dosing.

Materials: USP grade raw materials was used whenever possible. Two solutions, the active ASO mixture, and filtered USP Water for washing were prepared prior to production. The two solutions were formulated as follows: 1) 12.5% polyethylene glycol (PEG), 12.5% polyvinyl pyrrolidone (PVP), 0.1M sodium acetate, pH 5.6 and 2) 15 mg/ml poly-L-lysine. Both solutions were filtered through a 0.2 μm filter into autoclaved bottles in a laminar flow hood. The active ASO cocktail was prepared by resuspending the individual ASO powders (HuCD40, HuCD80, and HuCD86) in Nuclease-Free Water and determining the concentration. The individual ASO solutions were mixed in an equimolar ratio and diluted to a concentration of 2.7 mM (27.45 mg/ml).

Environment/Process Cleaning: The ASO MS product was produced in an ISO 8 (Class 100,000) cleanroom. The maximum process closure was maintained as permissible. Any process operation that required exposure to the environment was conducted in a laminar flow hood in the cleanroom. Calibration and certification of HVAC systems and the utility instrumentation will remain current. Preventative maintenance programs for the clean rooms and associated utilities was performed according to established procedures. Routine cleaning and sanitization of the clean rooms was in effect and full gowning was implemented during the campaign.

Product contact equipment and components were purchased sterile, or sanitized in the laboratory autoclave for ≧30 minutes at 121° C., or sanitized using sodium hydroxide and USP-Purified Water. Disposable, sterile components were used when possible. Non-product contact surfaces were sanitized using 70% Isopropanol and Spor-Klenz Cold-Sterilant.

Sample (Test and/or Control) Description: The following tests (Table 4 below) were run to characterize the material.

TABLE 4

| Test | Method | Target Specifications |
|---|---|---|
| Identity (3 ASOs) | IPRP-HPLC | 33 ± 6% (each ASO) |
| Assay (Total ASO) | UV Spectrophotometry | 0.65-0.78 mg/mg |
| Assay PLL | Amino Acid Analysis | 0.22-0.30 mg/mg |
| PEG 3350 Content | RP-HPLC/ELSD | <10 μg/mg |
| PVP K30 Content | RP-HPLC/ELSD | <10 μg/mg |
| Moisture Content | Karl Fischer | Report |
| Sodium Content | Atomic Adsorption | <10 μg/mg |
| Particle Size Distribution | Laser Diffraction - Sympatec | $V_{50}$ 1-5 microns |
| Particle Size Distribution | Time of Flight - Aerosizer | Report |

TABLE 4-continued

| Test | Method | Target Specifications |
|---|---|---|
| Particle Size Morphology | SEM | Report |
| Bioburden | USP <85> | Report |
| End toxin | USP <61> | Report |

Example 7

Additional pre-clinical studies were conducted in order to demonstrate that microsphere-AS-ODN (comprising the antisense sequences SEQ ID NOs. 4 6 and 7 described in Example 4) is non-toxic in non-human primates, as well as to confirm the pancreatic lymph node trafficking and accumulation of radiolabeled or fluorescence-tagged oligonucleotides in microspheres.

Initial experiments utilized Invitrogen's commercially-available Fluospheres, which are contemplated to behave identically to the microspheres (MSP's) disclosed herein. Spleen and lymph nodes were isolated from study subjects that exhibited accumulated MSP's to identify the cell types that take them up, as well as their functional capacity.

Results from these experiments showed that the microsphere-AS-ODN is non-toxic and that accumulation of MSP's was seen in lymph nodes, pancreas, kidney, and liver. This accumulation of MSP's surprisingly mirrored, at least in part, what was observed in similar experiments using the mouse.

Example 8

Figure 20:
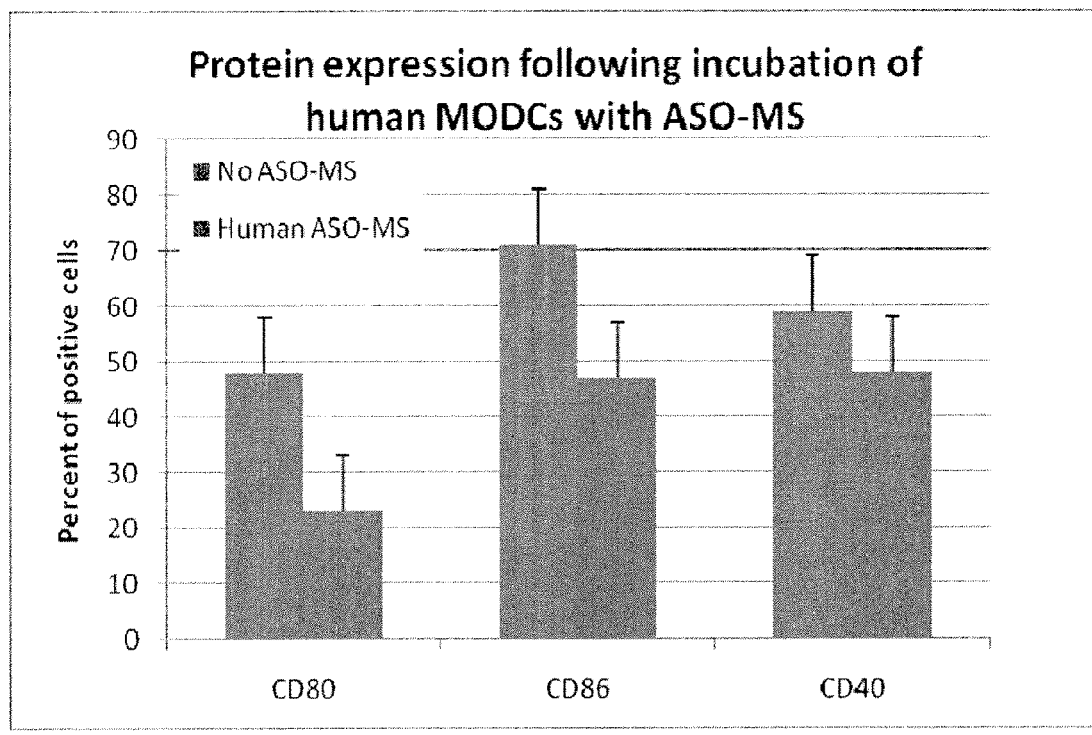
FIG. 20 depicts the protein expression following incubation of human monocyte-derived dendritic cells with ASO-MS.
Figure 21:
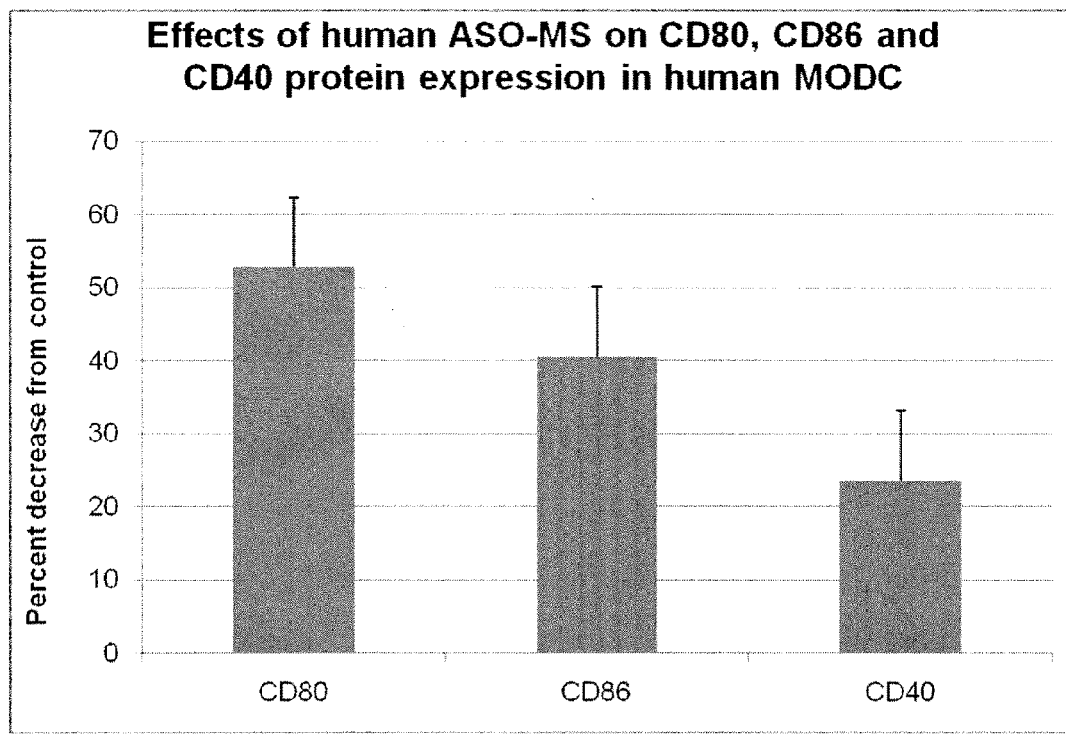
FIG. 21 shows the percent decrease in protein expression following culture with human ASO-MS.

Protein Knock-down of ASO-MS targets. Monocyte-derived dendritic cells were generated by centrifugation over a Ficoll gradient, adherence of monocytes to plastic and differentiation of cells in the presence of IL-4 and GM-CSF for 7 days. After 7 days, human ASO-MS (final concentration—20 μg/ml, sequences set out in SEQ ID NOs. 4, 6 and 7 as described in Example 4) or media alone was added to cells. Cells were cultured from 7-14 days and then collected for analysis by flow cytometry. Cells were incubated with antibodies directed against human CD80, human CD86, and human CD40 or corresponding isotype controls for 30 minutes at 4° C. and then washed with PBS/FCS buffer. Cells were resuspended in PBS/FCS buffer and analyzed on a FACSCalibur flow cytometer. The FACSCalibur is calibrated daily with Calibrite beads from BD Bioscience. Data was analyzed on CellQuest software for the percentage of cells that positive for each protein. Data is present as the average percent of positive cells in each group (FIG. 20) or the percent decrease from control/untreated cells (FIG. 21) +/−standard deviation, as calculated in Excel 2007. Cells from two different donors were analyzed on two different days of culture between the 7-14 day period.

The invention claimed is:

1. A method of treating or reversing type-1 diabetes in a mammal comprising administering a composition comprising microspheres in an amount effective to treat or reverse type-1 diabetes, said microspheres comprising oligonucleotides that are antisense to and targeted to bind to primary transcripts selected from the group consisting of CD40, CD80 and CD86 primary transcripts, said oligonucleotides individually comprising a polynucleotide sequence selected from the group consisting of SEQ ID NO: 4, SEQ ID NO: 5, SEQ ID NO: 6, SEQ ID NO: 7, and modified forms of SEQ ID NO: 4, SEQ ID NO: 5, SEQ ID NO: 6, and SEQ ID NO: 7 which target and bind CD40, CD80 and CD86 primary transcripts.

2. A process for protecting pancreatic beta cells of a mammal from autoimmune destruction, comprising administering to said mammal a composition comprising microspheres in an amount effective to protect pancreatic beta cells, said microspheres comprising oligonucleotides that are antisense to and targeted to bind to primary transcripts selected from the group consisting of CD40, CD80 and CD86 primary transcripts, and combinations thereof, said oligonucleotides individually comprising a polynucleotide sequence selected from the group consisting of SEQ ID NO: 4, SEQ ID NO: 5, SEQ ID NO: 6, SEQ ID NO: 7, and modified forms of SEQ ID NO: 4, SEQ ID NO: 5, SEQ ID NO: 6, and SEQ ID NO: 7 which target and bind CD40, CD80 and CD86 primary transcripts.

3. A method of decreasing T-cell-mediated pancreatic inflammation or pancreatic beta cell death in a mammal comprising administering to said mammal a composition comprising microspheres in an amount effective to decrease T-cell-mediated pancreatic inflammation or pancreatic beta cell death, said microspheres in said composition comprising oligonucleotides that are antisense to and targeted to bind to primary transcripts selected from the group consisting of CD40, CD80 and CD86 primary transcripts, and combinations thereof, said oligonucleotides individually comprising a polynucleotide sequence selected from the group consisting of SEQ ID NO: 4, SEQ ID NO: 5, SEQ ID NO: 6, SEQ ID NO: 7, and modified forms of SEQ ID NO: 4, SEQ ID NO: 5, SEQ ID NO: 6, and SEQ ID NO: 7 which target and bind CD40, CD80 and CD86 primary transcripts.

4. A method of preserving residual beta cell mass in a mammal with new-onset or preclinical autoimmune diabetes comprising administering to said mammal a composition comprising microspheres in an amount effective to preserve residual beta cell mass wherein administration of the composition maintains the beta cell mass of the mammal to at least about 15% of the mass present prior to diabetes onset, said microspheres in said composition comprising oligonucleotides that are antisense to and targeted to bind to primary transcripts selected from the group consisting of CD40, CD80 and CD86 primary transcripts and combinations thereof, said oligonucleotides individually comprising a polynucleotides sequence selected from the group consisting of SEQ ID NO: 4, SEQ ID NO: 5, SEQ ID NO: 6, and SEQ ID NO: 7, and modified forms of SEQ ID NO: 4, SEQ ID NO: 5, SEQ ID NO: 6, and SEQ ID NO: 7 which target and bind CD40, CD80 and CD86 primary transcripts.

5. A pharmaceutical composition comprising antisense oligonucleotides individually having the polynucleotide sequences set out in SEQ ID NO: 4, SEQ ID NO: 6 and SEQ ID NO: 7, polynucleotide sequences having at least 75% polynucleotide sequence homology to SEQ ID NO: 4, SEQ ID NO: 6 and SEQ ID NO: 7 and which target and bind human CD40, CD80 and CD86 primary transcripts, or modified forms SEQ ID NO: 4, SEQ ID NO: 6 and SEQ ID NO: 7 and which target and bind human CD40, CD80 and CD86 primary transcripts.

6. The pharmaceutical composition of claim 5, comprising antisense oligonucleotides individually having at least 80% polynucleotide sequence homology to SEQ ID NO: 4, SEQ ID NO: 6 and SEQ ID NO: 7 and which target and bind human CD40, CD80 and CD86 primary transcripts.

7. The pharmaceutical composition of claim 5, comprising antisense oligonucleotides individually having at least 85% polynucleotide sequence homology to SEQ ID NO: 4, SEQ ID NO: 6 and SEQ ID NO: 7 and which target and bind human CD40, CD80 and CD86 primary transcripts.

8. The pharmaceutical composition of claim 5, comprising antisense oligonucleotides individually having at least 90% polynucleotide sequence homology to SEQ ID NO: 4, SEQ ID NO: 6 and SEQ ID NO: 7 and which target and bind human CD40, CD80 and CD86 primary transcripts.

9. The pharmaceutical composition of claim 5, comprising antisense oligonucleotides individually having at least 95% polynucleotide sequence homology to SEQ ID NO: 4, SEQ ID NO: 6 and SEQ ID NO: 7 and which target and bind human CD40, CD80 and CD86 primary transcripts.

10. A pharmaceutical composition comprising antisense oligonucleotides individually having the polynucleotide sequences set out in SEQ ID NO: 4, SEQ ID NO: 5 and SEQ ID NO: 6, polynucleotide sequences having at least 75% polynucleotide sequence homology to SEQ ID NO: 4, SEQ ID NO: 5 and SEQ ID NO: 6 and which target and bind human CD40, CD80 and CD86 primary transcripts, or modified forms of SEQ ID NO: 4, SEQ ID NO: 5 and SEQ ID NO: 6 and which target and bind human CD40, CD80 and CD86 primary transcripts.

11. The pharmaceutical composition of claim 10, comprising antisense oligonucleotides individually having at least 80% polynucleotide sequence homology to SEQ ID NO: 4, SEQ ID NO: 5 and SEQ ID NO: 6 and which target and bind human CD40, CD80 and CD86 primary transcripts.

12. The pharmaceutical composition of claim 10, comprising antisense oligonucleotides individually having at least 85% polynucleotide sequence homology to SEQ ID NO: 4, SEQ ID NO: 5 and SEQ ID NO: 6 and which target and bind human CD40, CD80 and CD86 primary transcripts.

13. The pharmaceutical composition of claim 10, comprising antisense oligonucleotides individually having at least 90% polynucleotide sequence homology to SEQ ID NO: 4, SEQ ID NO: 5 and SEQ ID NO: 6 and which target and bind human CD40, CD80 and CD86 primary transcripts.

14. The pharmaceutical composition of claim 10, comprising antisense oligonucleotides individually having at least 95% polynucleotide sequence homology to SEQ ID NO: 4, SEQ ID NO: 5 and SEQ ID NO: 6 and which target and bind human CD40, CD80 and CD86 primary transcripts.

15. The pharmaceutical composition of claim 5 or claim 10, wherein said oligonucleotides are formulated in microspheres.

* * * * *